United States Patent [19]
Hora et al.

[11] Patent Number: 5,730,969
[45] Date of Patent: Mar. 24, 1998

[54] METHOD AND COMPOSITIONS FOR SOLUBILIZATION AND STABILIZATION OF POLYPEPTIDES, ESPECIALLY PROTEINS

[75] Inventors: Maninder Singh Hora, Rodeo; Joseph Rubinfeld, Danville, both of Calif.; Warren Stern, Gainesville, Fla.; Gregory J. Wong, San Leandro, Calif.

[73] Assignee: Chiron Corporation, Emeryville, Calif.

[21] Appl. No.: 474,178

[22] Filed: Jun. 7, 1995

Related U.S. Application Data

[60] Division of Ser. No. 373,928, Jun. 29, 1989, which is a continuation-in-part of Ser. No. 253,720, Oct. 5, 1988, abandoned.

[51] Int. Cl.⁶ .................. A61K 38/17; A61K 38/19; A61K 38/20; A61K 38/49
[52] U.S. Cl. .................. 424/85.1; 424/85.2; 424/85.4; 424/85.6; 424/94.3; 514/2; 514/3; 514/12; 514/21
[58] Field of Search .................. 435/188; 424/85.1, 424/85.2, 85.4, 85.5, 85.6, 85.7, 94.3; 530/303, 351, 399; 514/2, 3, 12, 21

[56] References Cited

U.S. PATENT DOCUMENTS

| 3,459,731 | 8/1969 | Gramera et al. | 260/209 |
|---|---|---|---|
| 4,024,223 | 5/1977 | Noda et al. | 424/180 |
| 4,228,160 | 10/1980 | Szejtli et al. | 424/180 |
| 4,232,009 | 11/1980 | Hayashi et al. | 424/180 |
| 4,351,846 | 9/1982 | Matsumoto et al. | 424/305 |

(List continued on next page.)

FOREIGN PATENT DOCUMENTS

| 1222697 | 6/1987 | Canada. |
|---|---|---|
| 0094157 | 11/1983 | European Pat. Off.. |
| 0123291 | 10/1984 | European Pat. Off.. |
| 0133767 | 3/1985 | European Pat. Off.. |
| 0149197 | 7/1985 | European Pat. Off.. |
| 0231132 | 8/1987 | European Pat. Off.. |
| 0335545 | 10/1989 | European Pat. Off.. |
| 62-164701 | 7/1978 | Japan. |
| 59/104556 | 6/1984 | Japan. |
| 61/070996 | 4/1986 | Japan. |
| 61/197602 | 9/1986 | Japan. |
| 61/236802 | 10/1986 | Japan. |
| 61/287901 | 12/1986 | Japan. |
| 61/287902 | 12/1986 | Japan. |
| 62-106901 | 5/1987 | Japan. |
| 62/223129 | 10/1987 | Japan. |
| 62/281855 | 12/1987 | Japan. |
| 63/027440 | 2/1988 | Japan. |
| 63/036793 | 2/1988 | Japan. |
| 63/135402 | 6/1988 | Japan. |
| 85/02767 | 7/1985 | WIPO. |

OTHER PUBLICATIONS

Molecular Pharmacology, vol. 32, Issued Jul. 1987, Laurenza et al, "Stimulation of Adenylate Cyclase . . . ", pp. 133–139.
Hagenlocher and Pearlman, Pharm. Res. 6:S30 (1989).
Loftsson et al, Eur. J. Pharm. Sci. 1:95 (1993).
Pitha and Hoshino, Int. J. Pharm. 80:243 (1992).
Kraus et al, Pharm. Ztg. Wiss. 136/4:11 (1991).
Manning et al, Pharm. Res. 6:903 (1989).
Johnson et al, J. Pharm. Sci. 83:1142 (1994).
Brewster et al, Int. J. Pharm. 75:R5 (1991).
Brewster et al, J. Parent. Sci. Technol. 43:231 (1989).
Brewster et al, J. Pharm. Sci. 77:981 (1988).

(List continued on next page.)

Primary Examiner—Jeffrey E. Russel
Attorney, Agent, or Firm—Burns, Doane, Swecker & Mathis, L.L.P.

[57] ABSTRACT

The invention provides a method for the solubilization and/or stabilization of polypeptides, especially proteins, using a cyclodextrin selected from the group consisting of hydroxypropyl, hydroxyethyl, glucosyl, maltosyl and maltotriosyl derivatives of β- and γ-cyclodextrin. Solubilized and/or stabilized compositions comprising a polypeptide, especially a protein, and the selected cyclodextrin are also described.

79 Claims, 4 Drawing Sheets

U.S. PATENT DOCUMENTS

| | | | |
|---|---|---|---|
| 4,352,793 | 10/1982 | Yamahira et al. | 424/180 |
| 4,383,992 | 5/1983 | Lipari | 424/238 |
| 4,407,795 | 10/1983 | Nicolau et al. | 424/180 |
| 4,424,209 | 1/1984 | Tuttle | 424/180 |
| 4,425,336 | 1/1984 | Tuttle | 424/180 |
| 4,438,106 | 3/1984 | Wagu et al. | 424/180 |
| 4,457,916 | 7/1984 | Hayashi et al. | 424/101 |
| 4,474,811 | 10/1984 | Masuda et al. | 424/317 |
| 4,478,995 | 10/1984 | Shinoda et al. | 536/46 |
| 4,479,944 | 10/1984 | Hayashi et al. | 424/180 |
| 4,479,966 | 10/1984 | Hayashi et al. | 424/305 |
| 4,497,803 | 2/1985 | Harada et al. | 514/450 |
| 4,499,085 | 2/1985 | Masuda | 514/58 |
| 4,505,893 | 3/1985 | Mori et al. | 424/94 |
| 4,518,588 | 5/1985 | Szejtli et al. | 514/58 |
| 4,524,068 | 6/1985 | Szejtli et al. | 514/58 |
| 4,552,760 | 11/1985 | Murakami et al. | 424/94 |
| 4,555,504 | 11/1985 | Jones | 514/26 |
| 4,565,807 | 1/1986 | Uekama et al. | 514/58 |
| 4,568,544 | 2/1986 | Hasegawa et al. | 424/94 |
| 4,575,548 | 3/1986 | Ueda et al. | 536/46 |
| 4,596,795 | 6/1986 | Pitha | 514/58 |
| 4,598,070 | 7/1986 | Ohwaki et al. | 514/58 |
| 4,603,123 | 7/1986 | Chiesi et al. | 514/58 |
| 4,608,366 | 8/1986 | Hasegawa et al. | 514/58 |
| 4,623,641 | 11/1986 | Szejtli et al. | 514/58 |
| 4,659,696 | 4/1987 | Hirai et al. | 514/15 |
| 4,663,316 | 5/1987 | Ninger et al. | 519/99 |
| 4,675,395 | 6/1987 | Fukazawa et al. | 536/103 |
| 4,727,064 | 2/1988 | Pitha | 514/58 |
| 4,728,509 | 3/1988 | Shimizu et al. | 424/81 |
| 4,728,510 | 3/1988 | Shibanai et al. | 424/94.5 |
| 4,751,095 | 6/1988 | Karl et al. | 426/548 |
| 4,764,604 | 8/1988 | Muller | 536/103 |
| 4,897,472 | 1/1990 | Korpela et al. | 536/46 |
| 4,925,678 | 5/1990 | Ranney | 424/493 |
| 4,983,586 | 1/1991 | Bodor | 514/58 |
| 5,002,935 | 3/1991 | Bodor | 514/58 |
| 5,120,720 | 6/1992 | Pitha et al. | 514/58 |
| 5,580,856 | 12/1996 | Prestrelski et al. | 514/21 |

OTHER PUBLICATIONS

Uekama, 1987, *Topics in Pharmaceutical Sciences*, 181–194.
Okada et al., 1988, *Chem. Pharm. Bull.* 36:2176–2185.
Kyoka et al., 1987, *Chem. Pharm. Bull.* 35:3413–3418.
Yamamoto et al., 1989, *Intl. Journal of Pharmaceutics* 49:163–171.
Wang et al., 1988, *Parenteral Formulations of Proteins and Peptides: Stability and Stabilizers* 42:2S–S26.
Uekama, Mar., 1985, *Pharmacy International*, 61–65.
Pitha, 1984, *J. Inclusion Phenomena* 2:477–485.
Fenyvesi, 1984, *Chem. Pharm. Bull.* 32(2):665–669.
Uekama et al., 1985, *International Journal of Pharmaceutics* 23:35–42.
Pitha et al., 1985, *J. Pharmaceutical Sciences* 74(9):987–990.
Pitha et al., 1986, *International J. Pharmaceutics* 29:73–82.
Uekama et al., 1987, *CRC Critical Reviews in Therapeutic Drug Carrier Systems* 3(1):1–40.
Okada et al., 1988, *Chem. Pharm. Bull.* 36(6):2176–2185.
Matsuyama et al., 1987, *Drug Development and Industrial Pharmacy* 13(15):2687–2691.
*Grant and Hackh's Chemical Dictionary*, fifth edition, 431(1987).
Brewster et al., *Pharmaceutical Res.*, vol. 8, No. 6, 792–795 (1991).
*Derwent Chemical Patent Index/Documentation Abstracts Journal*, Week 7948, 86688B (1979), abstract of JP 54/135215, published Oct. 1979.
*Chem. Abstracts*, vol. 99, 500, 120601n (1983), abstract of JP 58/092691 published Jun. 1983.
*Derwent Chemical Patent Index/Documentation Abstracts Journal*, Week 8528, 169436 (1985), abstract of JP 60/100524, published Jun. 1985.
*Derwent Chemical Patent Index/Documentation Abstracts Journal*, Week 8545, 279148 (1985), abstract of JP 60/188067, published Sep. 1985.
*Derwent Chemical Patent Index/Documentation Abstracts Journal*, Week 8632, 207158 (1986), abstract of JP 61/137827, published Jun. 1986.
*Chemical Abstracts*, vol. 110, No. 14, abstract No. 121420k, abstract of JP 63/115821 (1989).

METHOD AND COMPOSITIONS FOR SOLUBILIZATION AND STABILIZATION OF POLYPEPTIDES, ESPECIALLY PROTEINS

CROSS-REFERENCE TO RELATED APPLICATION

This application is a divisional of application Ser. No. 07/373,928, filed Jun. 29, 1989, which is a continuation-in-part of applicants' application Ser. No. 07/253,720, filed Oct. 5, 1988, now abandoned, incorporated by reference herein in its entirety and relied upon.

FIELD OF THE INVENTION

The present invention relates to a method for the solubilization and/or stabilization of polypeptides, especially proteins, by means of selected cyclodextrin derivatives. Solubilized and/or stabilized compositions comprising a polypeptide, especially a protein, and selected cyclodextrin derivatives are also described.

BACKGROUND OF THE INVENTION

Cyclodextrins are cyclic oligosaccharides. The most common cyclodextrins are α-cyclodextrin, which is composed of a ring of six glucose residues; β-cyclodextrin, which is composed of a ring of seven glucose residues; and γ-cyclodextrin, which is composed of a ring of eight glucose units. The inside cavity of a cyclodextrin is lipophilic, while the outside of the cyclodextrin is hydrophilic; this combination of properties has led to widespread study of the natural cyclodextrins, particularly in connection with pharmaceuticals, and many inclusion complexes have been reported. β-Cyclodextrin has been of special interest because of its cavity size, but its relatively low aqueous solubility (about 1.8% w/v at 25° C.) and attendant nephrotoxicity have limited its use in the pharmaceutical field.

Attempts to modify the properties of the natural cyclodextrins have resulted in the development of heptakis (2,6-di-O-methyl)-β-cyclodextrin, heptakis (2,3,6-tri-O-methyl)-β-cyclodextrin, hydroxypropyl-β-cyclodextrin, β-cyclodextrin-epichlorohydrin polymer and others. For a comprehensive review of cyclodextrins and their use in pharmaceutical research, see Pitha et al, in *Controlled Drug Deliver*, ed. S. D. Bruck, Vol. I, CRC Press, Boca Raton, Fla., pp. 125–148 (1983). For an even more recent overview, see Uekama et al, in *CRC Critical Reviews in Therapeutic Drug Carrier Systems*, Vol. 3 (1), 1–40 (1987); Uekama, in *Topics in Pharmaceutical Sciences* 1987, eds. D. D. Breimer and P. Speiser, Elsevier Science Publishers B.V. (Biomedical Division), 181–194 (1987); and Pagington, *Chemistry in Britain*, pp. 455–458 (May 1987).

Inclusion complexes of α-, β- or γ-cyclodextrin or their mixtures with a variety of drugs have been described by numerous parties and various advantages have been attributed to the complexes. These descriptions include the following:

| INVENTOR | U.S. PAT. NO. | ACTIVE INGREDIENT | USE | ADVANTAGE |
|---|---|---|---|---|
| Noda et al | 4,024,223 | menthol &/or methyl salicylate | antiphlogistic, analgesic | reduced unpleasant odor, increased wet packing effect |
| Szejtli et al | 4,228,160 | indomethacin | anti-inflammatory, protective during pregnancy | reduced ulcerative effect |
| Hayashi et al | 4,232,009 | ω-halo-PGI$_2$ analogs | hypotensive, uterine contraction stimulating, blood platelet aggregation inhibiting | increased stability |
| Matsumoto et al | 4,351,846 | 3-hydroxy- and 3-oxo-prostaglandin analogs | uterine contraction stimulating | increased stability |
| Yamahira et al | 4,352,793 | bencyclane fumarate | anti-convulsant, vasodilative | increased stability at strong acid pH, faster gastric emptying, higher blood concentrations, less irritation, improved hemolytic activity |
| Lipari | 4,383,992 | steroids—corticosteroids, androgens, anabolic steroids, estogens, progestagens | hormonal | improved water solubility, increased therapeutic response in eye |
| Nicolau | 4,407,795 | p-hexadecyl-aminobenzoic acid sodium salt | antiatherosclerotic | enhanced bioavailability |
| Tuttle[1] | 4,424,209 | 3,4-diisobutyryloxy-N-[3-(4-isobutyryloxy-phenyl)-1-methyl-n-propyl]-β-phenethylamine | cardiac contractility agent | |
| Tuttle | 4,425,336 | 3,4-dihydroxy-N-[3-(4-hydroxyphenyl)-1-methyl-n-propyl]-β-phenethylamine | cardiac contractility agent | capable of oral administration |
| Wagu et al | 4,438,106 | EPA and DHA (fatty acids) | | deodorized, storage stable |
| Masuda et al[2] | 4,474,811 | 2-(2-fluoro-4-biphenylyl)propionic acid or salt | anti-inflammatory ophthalmic | reduced eye irritation, higher concentrations, no side effects, highly soluble, long stability, excellent pharmacological effects |
| Shinoda et al | 4,478,995 | acid addition salt of (2'-benzyloxycarbonyl)phenyl trans-4-guanidinomethyl-cyclohexane-carboxylate | anti-ulcer | excellent water solubility, good absorption in digestive tract, good anti-ulcer activity |
| Hayashi et al | 4,479,944 | PGI$_2$ analog | for treatment of artereosclerosis, cardiac | stabilization against decomposition |

-continued

| INVENTOR | U.S. PAT. NO. | ACTIVE INGREDIENT | USE | ADVANTAGE |
|---|---|---|---|---|
| Hayashi et al | 4,479,966 | 6,9-methano-PGI$_2$ analogs | failure or thrombosis for hypertension, cerebral thrombosis and the like | increased stability |
| Harada et al | 4,497,803 | lankacidin-group antibiotic | antibiotic for swine dysentery | enhanced water solubility and stability, increased rate and amount of absorption |
| Masuda | 4,499,085 | prostaglandin analog | treating anoxia of brain cells | |
| Szejtli et al | 4,518,588 | phendiline, i.e. N-(1-phenyl-ethyl)-3,3-diphenylpropylamine or its hydrochloride | coronary dilator calcium antagonist | improved water solubility, accelerated and increased in vivo resorption & dissolution at pH/temperature of gastric acid |
| Szejtli et al | 4,524,068 | piperonyl butoxide | synergizes pesticidal effect of known insecticides and fungicides | easily handled crystalline solid; improved water solubility, increased absorption & velocity of penetration through biological membranes |
| Jones | 4,555,504 | a cardiac glycoside | cardiac effect | high aqueous solubility, apparently better bioavailability |
| Uekama et al[3] | 4,565,807 | pirprofen | anti-inflammatory, analgesic, antipyretic | improved stability to oxidation, freedom from bitter taste, less irritating |
| Ueda et al | 4,575,548 | 2-nitroxymethyl-6-chloropyridine | for vascular disorders | non-volatile powder vs. volatile oil |
| Ohwaki et al[4] | 4,598,070 | tripamide | anti-hypertensive | improved solubility |
| Chiesi et al | 4,603,123 | piroxicam, i.e. 4-hydroxy-2-methyl-N-2-pyridyl-2H-1,2-benzothiazine-3-carboxamide-1,1-dioxide | anti-inflammatory, analgesic | |
| Hasegawa et al | 4,608,366 | mobenzoxamine, i.e. 1-[2-(4-methoxy-benzhydryloxy)ethyl]-4-[3-(4-fluorobenzoyl)propyl]-piperazine | antiemetic, anti-spasmodic | storage stability better absorption through digestive tract |
| Hirai et al[2] | 4,659,696 | polypeptide | | improving drug absorption by non-oral and non-injection routes |
| Szejtli et al | 4,623,641 | PGI$_2$ methyl ester | anti-ulcer | improved storage stability |
| Ninger et al | 4,663,316 | unsaturated phosphorus-containing | antibiotic, antifungal, antitumor | enhanced stability against oxidation |
| Fukazawa et al | 4,675,395 | antibiotics, including phosphotrienin hinokitiol | bactericidal, bacteriostatic | improved water solubility, less odor |
| Shimizu et al | 4,728,509 | 2-amino-7-isopropyl-5-oxo-5H-[1]-benzopyrano-[2,3-b]pyridine-3-carboxylic acid | anti-allergic, anti-inflammatory | improved water solubility to increase concentration to therapeutic levels in nasal drops and eye drops |
| Shibanai et al[6] | 4,728,510 | a milk component | bath preparation | improved stability |
| Karl et al | 4,751,095 | aspartame | dipeptide sweetener | stabilization from hydrolysis |

[1]Tuttle also describes use of 2,6-di-O-methyl-β-cyclodextrin and 2,3,6-tri-O-methyl β-cyclodextrin to form the inclusion complex.
[2]This may not be an inclusion complex, but simply a physical mixture.
[3]This is a mixture and/or an inclusion compound.
[4]The inventors also mention prior known solubility improvements of cyclodextrin inclusions of barbituric acid derivatives, mefenamic acid, indomethacin and chloramphenicol.
[5]The inventors refer to this as an "occlusion" compound.
[6]The inventors also mention a derivative of cyclodextrin and a cyclodextrin-containing starch decomposition product for use in forming the clathrate.

Among the patents listed above, only Hirai et al U.S. Pat. No. 4,659,696 appears to relate to proteins or polypeptides. It would appear from the claims of the Hirai et al patent, however, that an inclusion complex is not formed and that what the invention provides is a pharmaceutical composition consisting essentially of a physical mixture of a hydrophilic, physiologically active polypeptide and cyclodextrin, said composition being a uniform mixture in dosage form. The cyclodextrin may be α-, β- or γ-cyclodextrin, or a cyclodextrin derivative, exemplified by tri-O-methylcyclodextrin and triaminocyclodextrin, α-cyclodextrin being particularly preferred. The physiologically active peptide may be thyrotropin releasing hormone, luteinizing hormone-releasing hormone, insulin, somatostatin, growth hormone, prolactin, adrenocorticotrophic hormone, melanocyte stimulating hormone, or many others. The composition is designed for nasal, vaginal or rectal preparation, i.e. a non-oral or non-injectable route of administration is used.

Matsuyama et al, *Drug Development and Industrial Pharmacy*, 13(15), 2687–2691 (1987), have reported on the thermodynamics of binding aromatic amino acids to α-, β- and γ-cyclodextrin. Human serum albumin, which contains aromatic amino acids, was also tested as a protein model. The authors suggest that cyclodextrins may protect peptides from enzymatic hydrolysis. Also, according to Sekisui Chemical Co., Ltd.'s Japanese Kokai Tokkyo Koho JP 59/104556 (84/104556), published Jun. 16, 1984, cyclized oligosaccharides such as β-cyclodextrin have been recently used in protein stabilizers which prevent denaturation of proteins and enzymes in blood. Human blood mixed with octylphenoxypoly(ethoxyethanol) and β-cyclodextrin was maintained for 24 hours with little change.

Inclusion complexes of 2,6-di-O-methyl-β-cyclodextrin with dibenzo[bd]pyran derivatives and salts having analgesic, antiemetic and narcosis-potentiating activities have been described in Nogradi et al U.S. Pat. No. 4,599,327; increased water solubility and thus improved biological activity have been claimed for the complexes. A review of the pharmaceutical applications of such methylated cyclodextrins has been published by Uekama, *Pharm. Int.*, March 1985, 61–65; see also Pitha, *Journal of Inclusion Phenomena* 2, 477–485 (1984).

Cyclodextrin polymer has been reported by Fenyvesi et al, *Chem. Pharm. Bull.* 32 (2), 665–669 (1984) to improve the dissolution of furosemide. Improvements in the dissolution and absorption of phenytoin using a water-soluble β-cyclodextrin epichlorohydrin polymer have been described by Uekama et al, *International Journal of Pharmaceutics*, 23, 35–42 (1985).

Hydroxypropyl-β-cyclodextrin (HPBCD or HPCD) and its preparation by propylene oxide addition to β-cyclodextrin were described in Gramera et al U.S. Pat. No. 3,459,731 nearly 20 years ago. Gramera et al also described the analogous preparation of hydroxyethyl-β-cyclodextrin by ethylene oxide reaction with β-cyclodextrin. Much more recently, Pitha and co-workers have described the improved preparation of this cyclodextrin derivative and its effects on the dissolution of various drug molecules. Pitha U.S. Pat. No. 4,596,795, dated Jun. 24, 1986, describes inclusion complexes of sex hormones, particularly testosterone, progesterone, and estradiol, with specific cyclodextrins, preferably hydroxypropyl-β-cyclodextrin and poly-β-cyclodextrin. The complexes enable the sex hormones to be successfully delivered to the systemic circulation via the sublingual or buccal route; the effectiveness of this delivery is believed to be due to "the high dissolution power of hydrophilic derivatives of cyclodextrins, the non-aggregated structure of their complexes with steroids, and their low toxicity and irritancy of mouth tissue". Success with other cyclodextrins, including poly -γ-cyclodextrin and hydroxypropyl-γ-cyclodextrin, have also been noted in the Pitha patent. See also Pitha et al, *J. Pharm. Sci.*, Vol. 74, No. 9, 987–990 (September 1985), concerning the same and related studies. Pitha et al also describe in the *J. Pharm. Sci.* article the storage stability of tablets containing a testosterone-hydroxypropyl-β-cyclodextrin complex and the lack of toxicity of the cyclodextrin itself, as well as the importance of the amorphous nature of the cyclodextrin derivatives and their complexes with drugs in improving dissolution properties.

The improved, optimized preparation and purification of hydroxypropyl-β-cyclodextrin have been recently described by Pitha et al, *International Journal of Pharmaceutics* 29, 73–82 (1986). In the same publication, the authors have described increased water solubility for 32 drugs in concentrated (40 to 50%) aqueous solutions of hydroxypropyl-β-cyclodextrin; improved solubilization of acetaminophen, apomorphine, butylated hydroxytoluene, chlorthalidone, cholecalciferol, dexamethasone, dicumarol, digoxin, diphenylhydantoin, estradiol, estriol, ethinylestradiol-3-methyl ether, ethisterone, furosemide, hydroflumethiazide, indomethacin, iproniazid phosphate, 17-methyltestosterone, nitroglycerin, norethindrone, ouabain, oxprenolol, progesterone, retinal, retinoic acid (all trans and salt forms), retinol, spironolactone, sulpiride, testosterone and theophylline was noted. The authors indicated this to be an extension of their earlier work with hydroxypropyl-β-cyclodextrin, which was previously found effective for oral administration of the sex hormones to humans. Their later work reported in Pitha et al, *International Journal of Pharmaceutics* 29, 73–82 (1986), has also been very recently described in Pitha U.S. Pat. No. 4,727,064, dated Feb. 23, 1988. That patent claims a composition containing an amorphous complex of cyclodextrin and a drug, and a method of producing a stabilizing amorphous complex of a drug and a mixture of cyclodextrins comprising (1) dissolving an intrinsically amorphous mixture of cyclodextrin derivatives which are water soluble and capable of forming inclusion complexes with drugs in water; and (2) solubilizing lipophilic drugs into aqueous media to form a solution and form a solubilized drug/cyclodextrin complex. Work with numerous drugs has been reported in the patent, but none involves proteins or other peptides. The patent describes the preparation of various substituted amorphous cyclodextrins, including hydroxypropyl-β-cyclodextrin and hydroxypropyl-γ-cyclodextrin, the latter by analogous condensation of propylene oxide with γ-cyclodextrin.

Uekama et al, *CRC Critical Reviews in Therapeutic Drug Carrier Systems*, Vol. 3 (1), pp. 1–40 (1987), have described the characteristics of various cyclodextrins, including hydroxypropyl-β-cyclodextrin. The authors have presented data showing improved solubilization in water in the presence of 15 mg/mL of HPBCD for the drugs carmofur, diazepam, digitoxin, digoxin, flurbiprofen, indomethacin, isosorbide dinitrate, phenytoin, prednisolone, progesterone and testosterone. In a discussion of the metabolism and toxicity of cyclodextrins, Uekama et al have indicated that cyclodextrins at low-moderate concentrations (usually 3–8% w/v and higher) cause hemolysis, and that the methylated cyclodextrins have higher hemolytic activity than the natural cyclodextrins. Hydroxypropyl-β-cyclodextrin is said to cause hemolysis beginning at 4.5 mM. The authors have further indicated that parenteral administration of large doses of cyclodextrins should be avoided, but that "γ-cyclodextrin and hydroxypropyl-β-cyclodextrin seem to be useful in drug solubilization for injections and liquid preparations used for mucous membranes." Use with polypeptides such as proteins is not mentioned.

JANSSEN PHARMACEUTICA N.V.'s International Patent Application No. PCT/EP84/00417, published under International Publication No. WO85/02767 on Jul. 4, 1985, has described pharmaceutical compositions comprising inclusion compounds of drugs, which are unstable or only sparingly soluble in water, with partially etherified β-cyclodextrin derivatives having hydroxyalkyl and optionally additional alkyl groups. Among the cyclodextrin derivatives contemplated are hydroxypropyl-β-cyclodextrin and hydroxyethyl-β-cyclodextrin, while the drugs include non-steroidal anti-rheumatic agents, steroids, cardiac glycosides and derivatives of benzodiazepine, benzimidazole, piperidine, piperazine, imidazole and triazole. Preferred drugs include etomidate, ketoconazole, tubulazole, itraconazole, levocabastine and flunarizine. The pharmaceutical compositions of the invention include oral, parenteral and topical formulations, with 4 to 10% solutions of cyclodextrin derivatives being utilized to solubilize various drugs. Improved solubilities of indomethacin, digitoxin, progesterone, dexamethasone, hydrocortisone and diazepam using 10% HPBCD are shown, and an injectable formulation of diazepam in 7% HPBCD is specifically described. The relatively low cyclodextrin concentrations used reflect a desire to avoid or minimize the hemolytic effects observed at higher cyclodextrin concentrations.

Carpenter et al, *The Journal of Pediatrics*, 111, 507–512 (October 1987) describe intravenous infusion of 2-hydroxypropyl-β-cyclodextrin, prepared as a 5% solution in water, to treat severe hypervitaminosis A. It was found that, during infusion, circulating retinyl esters increased transiently, while total vitamin A excreted in the urine was enhanced after infusion. Thus, intravenous infusion of 5% HPBCD was found to decrease in vivo levels of the vitamin, presumably by complexing with the vitamin and removing some of the excess from the body.

Formulation of a particular dihydropyridine⇌pyridinium salt redox system for brain-specific delivery of estradiol "in a water-soluble β-hydroxy-cyclodextrin" is reported by Bodor and co-workers in Estes et al, "Use of a Chemical Redox System for Brain Enhanced Delivery of Estradiol Decreases Prostate Weight," in *Biological Approaches to the Controlled Delivery of Drugs*, ed. R. L. Juliano, Annals of the New York Academy of Sciences, Volume 507, 1987, 334–336.

JANSSEN PHARMACEUTICA N.V.'s European Patent Application No. 86200334.0, published under EPO Publication No. 0197571 on Oct. 15, 1986, describes γ-cyclodextrin derivatives which are γ-cyclodextrin substituted with $C_1$–$C_6$ alkyl, hydroxy $C_1$–$C_6$ alkyl, carboxy $C_1$–$C_6$ alkyl or $C_1$–$C_6$ alkyloxycarbonyl $C_1$–$C_6$ alkyl or mixed ethers thereof. Among the specific derivatives named are hydroxypropyl-γ-cyclodextrin and hydroxyethyl-γ-cyclodextrin. Compositions comprising the cyclodextrin derivatives and a drug are also described. See also corresponding Müller U.S. Pat. No. 4,764,604, dated Aug. 16, 1988.

The inclusion characteristics of yet other derivatized cyclodextrins have also been described in the literature. Studies of branched cyclodextrins which are glucosyl and maltosyl derivatives of α-, β- and γ-cyclodextrin and their inclusion complexes with drugs have recently been reported. Uekama, in *Topics in Pharmaceutical Sciences* 1987, eds. D. D. Breimer and P. Speiser, Elsevier Science Publishers B.V. (Biomedical Division), 181–194 (1987), has described the effects on bio-pharmaceutical properties of maltosyl and glucosyl cyclodextrin derivatives, including enhanced drug absorption. In that publication, Uekama again indicated that the natural cyclodextrins caused hemolysis in the order of γ<α<β. In the case of chemically modified cyclodextrins, the order changed to hydroxyethyl-β<maltosyl-β<hydroxypropyl-β<β<methyl-β.

Koizumi et al, *Chem. Pharm. Bull.* 35 (8), 3413–3418 (1987), have reported on inclusion complexes of poorly water-soluble drugs with glucosyl cyclodextrins, namely 6-O-α-D-glucosyl-α-CD ($G_1$-α-CD), 6-O-α-D-glucosyl-β-CD ($G_1$-β-CD) and 6A, $6^D$-di-O-α-D-glucosyl-β-CD ($2G_1$-β-CD).

Okada et al, *Chem. Pharm. Bull.*, 36 (6), 2176–2185 (1988), have reported on the inclusion complexes of poorly water-soluble drugs with maltosyl cyclodextrins, namely 6-O-α-maltosyl-α-CD ($G_2$-α-CD), 6-O-α-maltosyl-β-CD ($G_2$-β-CD), 6-O-α-maltosyl-γ-CD ($G_2$-γ-CD), 6-O-α-maltotriosyl-α-CD ($G_3$-α-CD), 6-O-α-maltotriosyl-β-CD ($G_3$-β-CD) and 6-O-α-maltotriosyl-γ-CD ($G_3$-γ-CD).

Yamamoto et al, in *International Journal of Pharmaceutics* 49, 163–171 (1989), have described physicochemical properties of branched β-cyclodextrins such as glucosyl-β-cyclodextrin, maltosyl-β-cyclodextrin and di-maltosyl-β-cyclodextrin, and their inclusion characteristics. Those authors report that the branched β-cyclodextrins are better solubilizers for poorly water-soluble drugs and have less hemolytic activity than β-cyclodextrin itself, and they suggest that glucosyl-β-cyclodextrin and maltosyl-β-cyclodextrin may be especially useful in parenteral preparations.

The patent literature reflects much recent work on the branched cyclodextrins carried out by Japanese workers, as discussed below. Japanese Kokai 63-135402 (TOKUYAMA SODA KK), published Jun. 7, 1988, describes compositions consisting of maltosyl-β-cyclodextrin and at least one of digitoxin, nifedipine, flulubiprophene, isosorbide nitrate, phenytoin, progesterone or testosterone. The compositions have improved water solubility and reduced erythrocyte destruction, are safe for humans and can be used as injections, eye drops, syrups, and for topical and mucous membrane application.

Japanese Kokai 62-281855 (DAIKIN KOGYO KK), published Dec. 7, 1987, describes stable, water-soluble inclusion compounds of maltosyl-β-cyclodextrin with a variety of vitamins and hormones, e.g. steroid hormones such as prednisolone, hydrocortisone and estriol. These lipophilic vitamins and hormones can thus be used as aqueous solutions.

Japanese Kokai 63-036793 (NIKKEN CHEM KK), published Feb. 17, 1988, describes the preparation of dimaltosyl-γ-cyclodextrin and its general use in medicines.

Japanese Kokai 62-106901 (NIKKEN CHEM KK), published May 18, 1987, describes the preparation of diglucosyl-β-cyclodextrin and its general use for pharmaceuticals.

Japanese Kokai 61-236802 (NIKKEN CHEM KK), published Oct. 22, 1986, describes the preparation of maltosyl-γ-cyclodextrin and its general use with drugs.

Japanese Kokai 61-197602 (NIKKEN CHEM KK), published Sep. 1, 1986, describes the preparation of maltosyl-β-cyclodextrin and its expected use in medicines.

Japanese Kokai 61-070996 (NIKKEN CHEM KK), published Apr. 11, 1986, describes the preparation of maltosyl-α-cyclodextrin and its general use in pharmaceuticals.

Japanese Kokai 63-027440 (SANRAKU OCEAN), published Feb. 5, 1988, describes compositions containing a water-insoluble or slightly soluble drug together with glucosylated branched cyclodextrin. Among the drugs mentioned are steroid hormones.

Japanese Kokai 62-164701 (SHOKUHIN SANGYO BIO), published Jul. 21, 1987, describes the preparation of diglucosyl-α-cyclodextrin and its general use in medicine.

Japanese Kokai 62-003795 (TOKUYAMA SODA KK), published Jan. 9, 1987, describes production of glucose and maltoligosaccharide (2–4 glucose units) derivatives of α-, β- and γ-cyclodextrin and their use as stabilizers for pharmaceuticals.

In recent years, there has been a tremendous increase in the number of products and potential products containing polypeptides, especially proteins, intended for therapeutic or diagnostic or analytical use. Typically, the proteins or other peptides are formulated in aqueous solution for injection or for use in diagnostic or analytical applications. Unfortunately, proteins often suffer from solubility and/or stability problems. Some proteins, for example, are not water-soluble. Others are soluble in water but still suffer from stability problems caused by protein degradation/denaturation, dimerization and/or polymerization, and the like, any of which may lead to inactivation. This seriously limits shelf-life and often imposes low-temperature storage requirements and restrictions on mechanical movement.

There are numerous causes of protein/peptide instability or degradation, including covalent bond reactions, such as hydrolysis, and the denaturation process. In the case of denaturation, the conformation or three-dimensional structure of the protein is disturbed and the protein unfolds from its usual globular structure. Rather than refolding to its natural conformation, hydrophobic interaction may cause clumping of molecules together, or aggregation, or it may cause refolding to an unnatural conformation. Either of these end results entails diminution or loss of biological activity.

For a summary of the causes of protein instability, see Wang et al, *Journal of Parenteral Science and Technology*, Technical Report No. 10, "Parenteral Formulations of Proteins and Peptides: Stability and Stabilizers", Supplement Volume 42, Number 25, 1988, pp. S3-S26.

The Wang et al publication referenced above also summarizes the art's use of various excipients to stabilize parenteral formulations of proteins and other peptides, including use of serum albumin, amino acids, fatty acids and phospholipids, surfactants, metals, polyols, reducing agents, metal chelating agents, polyvinylpyrrolidone, hydrolyzed gelatin and ammonium sulfate, including agents used as cryoprotectants, which prevent or lessen denaturation under freezing conditions or lyophilization, such as carbohydrates, alcohols, polyvinylpyrrolidone and glutamic acid. Examples of excipients proposed by the art for stabilizing specific proteins are described in Hayashi et al U.S. Pat. No. 4,457,916, issued Jul. 3, 1984, KYOWA HAKKO KOGYO CO, LTD.'s European Patent Publication No. 0123291 and E. I. DUPONT DE NEMOURS AND COMPANY'S European Patent Publication No. 0231132.

The Hayashi et al patent describes a method for stabilizing Tumor Necrosis Factor (TNF) by adding a stabilizing agent selected from a nonionic surfactant, at least one substance selected from D-glucose, D-galactose, D-xylose, D-glucuronic acid, a salt of D-glucuronic acid, trehalose, a dextran and a hydroxyethyl starch and mixtures thereof. The resultant aqueous solution or powder containing TNF is said to be capable of prolonged storage without loss of activity and stable on freezing, thawing, lyophilization, heat-treatment or the like.

European Patent Publication No. 0123291, published Oct. 31, 1984, describes a method for stabilizing interferon involving addition of an alkali metal salt or magnesium chloride to interferon, optionally including addition of serum albumin and freeze-drying to further enhance stability. The patent publication also describes a method for stabilizing interferon by contacting it with a saccharide selected from the group consisting of dextran, chondroitin sulfuric acid, starch, glycogen, insulin, dextrin and alginic acid salt.

European Patent Publication No. 0231132, published Aug. 5, 1987, relates to a recombinant interleukin-2 (IL-2) composition and process for making it. In discussing the prior art, the European publication refers to earlier European Patent Publication No. 0133767 as disclosing that gamma-interferon, obtainable from human leukocytes, can be stabilized by addition of albumin and/or a sugar. The sugars can include monosaccharides, disaccharides, sugar alcohols and mixtures thereof, e.g. glucose, mannose, galactose, fructose, sucrose, maltose, lactose, mannitol and xylitol. Also, European Patent Publication No. 0231132 acknowledges that protein (chymotrypsinogen and ribonuclease) stabilization using glycerol is reported by Gekko et al, *Biochemistry* 20, 4677–4686 (1981). European No. 0231132 itself relates to recombinant human IL-2 compositions comprising water, recombinant interleukin-2 and preferably a polyol. Suitable polyols are said to be water-miscible or water-soluble, for example polyhydroxy alcohols, monosaccharides and disaccharides including mannitol, glycerol, ethylene glycol, propylene glycol, trimethyl glycol, glucose, fructose, arabinose, mannose, maltose and sucrose. The polyol is said to increase the activity of the IL-2.

Despite the foregoing, there remains a clear and pressing need in this art for a more effective and generally applicable method and compositions for the solubilization and stabilization of polypeptides such as proteins.

SUMMARY OF THE INVENTION

The present invention provides a method and compositions for stabilizing and/or solubilizing polypeptides, especially proteins, by means of cyclodextrin selected from the group consisting of hydroxypropyl, hydroxyethyl, glucosyl, maltosyl and maltotriosyl derivatives of β- and γ-cyclodextrin. Thus, in one aspect, the invention provides a method for solubilizing and/or stabilizing a polypeptide, said method comprising combining said polypeptide with an effective solubilizing and/or stabilizing amount of cyclodextrin selected from the group consisting of hydroxypropyl, hydroxyethyl, glucosyl, maltosyl and maltotriosyl derivatives of β- and γ-cyclodextrin. Preferably, an aqueous solution comprising said cyclodextrin is employed. In another aspect, the present invention provides a composition, especially an aqueous composition, comprising a polypeptide and an effective solubilizing and/or stabilizing amount of cyclodextrin selected from the group consisting of hydroxypropyl, hydroxyethyl, glucosyl, maltosyl and maltotriosyl derivatives of β- and γ-cyclodextrin. In still another aspect, the invention provides a lyophilized composition comprising a polypeptide and an effective stabilizing amount of cyclodextrin selected from the group consisting of hydroxypropyl, hydroxyethyl, glucosyl, maltosyl and maltotriosyl derivatives of β- and γ-cyclodextrin. Preferably, the foregoing methods and compositions are directed toward improvements in biologically useful protein formulations.

BRIEF DESCRIPTION OF THE DRAWINGS

The objects and advantages of the present invention will be apparent from the following detailed description and accompanying drawings, in which.

DETAILED DESCRIPTION OF THE INVENTION

Figure 1:
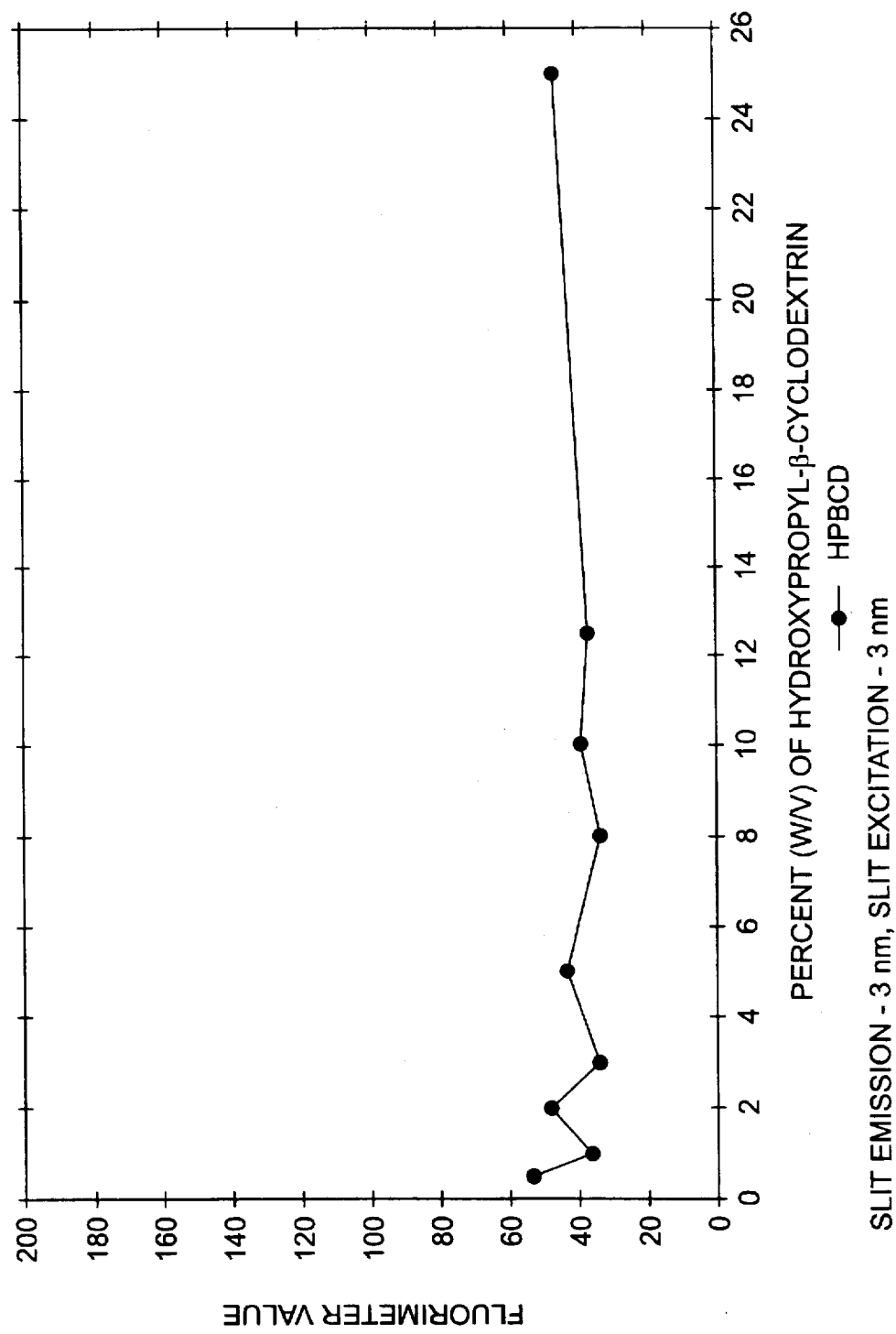
FIG. 1 is a plot of fluorimeter units as an indication of initial light scattering for samples of interleukin-2 (IL-2) in increasing concentrations (percent w/v) of hydroxypropyl-β-cyclodextrin (HPBCD)

The polypeptides intended for use according to the present invention are any polypeptides which are biologically or industrially useful. A biologically useful polypeptide in accord with this invention is any polypeptide which can be employed in the diagnosis, cure, mitigation, treatment or prevention of disease or in the enhancement of desirable physical or mental development and conditions in man or animals. Polypeptides, especially proteins, for use in human and/or veterinary medicine or in diagnosis (in vivo or in vitro.) are of particular interest. Industrially useful polypeptides are those employed analytically, in production or which are otherwise useful in chemical industry.

Amino acids are organic compounds that have at least one amino (—NH$_2$) group and at least one carboxyl (—COOH) group. Oligopeptides are amino acid oligomers which are formed by reacting amino and carboxyl groups from different amino acids to release a water molecule and form a peptide linkage. Polypeptides are amino acid polymers which are formed in the same way. Generally, oligopeptides have between 2 and 20 peptide linkages whereas polypeptides have more. Proteins are very large polypeptides. The amino acids which make up the polypeptides of the present invention may be natural or synthetic, may have the amino group attached to any noncarbonyl carbon atom (e.g., to the α, β, γ, δ or ε carbon as measured from the α-COOH group of the amino acid), may exist as enantiomers (e.g. D- or L-) or diasteriomers, may have blocked carboxyl or amino groups and may have side chains which are hydrophobic, hydrophilic, acidic, basic or neutral. The synthetic polypeptides may contain reversed peptide linkages, in which case they must contain at least one diamine and one dicarboxylic acid monomer.

The polypeptides intended for use in the methods and compositions of this invention include molecules to which nonpeptide prosthetic groups, such as carbohydrates, hemes and fatty acids, have been attached. The polypeptides include molecules made by living organisms or cells, molecules made by synthetic organic chemistry and molecules which are synthetically modified biological products. They may have an amino acid sequence identical to that of a natural substance or one altered by techniques such as site-directed mutagenesis.

In addition to the covalent (primary) structure, the polypeptides may possess unique conformations (combinations of secondary, tertiary and quaternary structure) which affect their biological function, aqueous solubility and ability to interact with the cyclodextrins. The polypeptides may have many biological functions. They may act as enzymes; enzyme inhibitors; antibodies; antigens; transporters of electrons, oxygen, metal ions, or small organic molecules; ionophores; antibiotics; mitogens; hormones; growth regulators; neurotransmitters; cell surface recognition proteins; cell chemotactic factors; and cytotoxins. They may also be receptors, agonists, antagonists of the following: ionophores, antibiotics, mitogens, hormones, neurotransmitters, growth regulators, cell surface recognition proteins, cell chemotactic factors and cytotoxins.

Uses for some of the preferred polypeptides of the invention include: immunization (as vaccine adjuvants), in vitro diagnostics (to increase the solubility/stability or lower the nonspecific binding of antigens or antibodies) and in vivo diagnostics and therapeutics (to increase the solubility/stability of therapeutic and diagnostic polypeptides). Preferred therapeutic targets of these polypeptides are cancers, such as melanoma, renal cell carcinoma, myeloma, leukemia, breast cancer, colorectal cancer, lymphoma, neuroblastoma, astrocytoma and glioma; auto-immune diseases, such as diabetes mellitus, rheumatoid arthritis and multiple sclerosis; immunodeficiency diseases; and infectious diseases.

Among the polypeptides contemplated by the present invention are therapeutically useful polypeptides such as anti-sera, anti-toxins and antigens. Anti-sera may include, for example, antirabies, antivenin (black widow spider venom), hepatitis B immune globulin, tetanus immune globulin, intravenous immune globulin, pertussis immune globulin and rabies immune globulin. Anti-toxins may include, for example, those for diphtheria and tetanus; Rho(D) immune globulin; serum components, such as 5% normal human serum albumin, 5% plasma protein fraction, 20% normal human serum albumin, 25% normal human serum albumin, factor II, factor VII, factor VIII, factor IX, factor X and Xa, antithrombin III, transferrin, haptoglobin, fibronectin, gamma globulins, protein C, protein S and thrombin; toxoids, such as diphtheria and tetanus; vaccines, including attenuated vaccines (such as those for cholera, influenza, meningitis, Yersinia pestis or plague, pneumonia, poliomyelitis, rabies, typhoid and staphyloccocus) and live vaccines (such as those for poliomyelitis, measles, rubella and mumps); growth factors, hormones and like bioactive peptides, as illustrated by α-1-antitrypsin, atrial natriuretic factor (diuretic), calcitonin, calmodulin, choriogonadotropin (α and β), colony stimulating factor, corticotropin releasing factor, β-endorphin, endothelial cell growth supplement, epidermal growth factor, erythropoietin, fibroblast growth factor, fibronectin, follicle stimulating hormone, granulocyte colony stimulating factor, growth hormone (somatotropin), growth hormone releasing factor (somatoliberin), insulin, insulin-like growth factor (somatomedin), an interferon (typically α, β, γ), an interleukin (typically 1, 2, 3, 4), lutropin, lymphotoxin, macrophage derived growth factor, macrophage inhibiting factor, macrophage stimulating factor, megakaryocyte stimulating factor, nerve growth factor, pancreatic endorphin, parathyroid hormone, platelet derived growth factor, relaxin, secretin, skeletal growth factor, superoxide dismutase, thymic hormone factor, thymic factor, thymopoeitin, thyrotropin, tissue plasminogen activator, transforming growth factor (α and β), tumor necrosis factor, tumor angiogenisis factor, vasoactive intestinal polypeptide and wound angiogenesis factor; immunosuppressives, such as RHO (D) ISG and IVGG's; thrombolytics such as urokinase, streptokinase and tissue plasminogen activator; and antigens such as Rhus all (poison ivy), Rhus tox poison ivy-polyvalent and staphage lysate (staphyloccocus lysate).

Other polypeptides contemplated by this invention are polypeptides specifically intended for veterinary use, including vaccines, animal growth factors and bovine interferons and interleukin-2. Illustrative vaccines include: bovine vaccines, for example those for anthrax, clostridium (multiple species), pasteurella, leptospira pomona, bovine diarrhea, brucillosis, parainfluenza, 3-respiratory syncytial virus, tetanus, vesicular stomatitis and staphylococcus; canine vaccines, for example those for bordetella, coronavirus, distemper, parvovirus, parainfluenza and rabies; equine vaccines, for example those for anthrax, encephalomyelitis, influenza, tetanus, rabies and streptococcus-strangles; feline vaccines, such as those for leukemia, pneumonitis-chlamydia and rabies; ovine vaccines, for example those for anthrax, blackleg, bluetongue, enterotoxemia, tetanus and vibriosis; and porcine vaccines, for example those for anthrax, enterotoxemia, dysentery, erysipelas, leptospirosis, parvovirus, pseudorabies, tetanus and rotavirus.

Yet other polypeptides contemplated by this invention have use in immunology. These include monoclonal antibodies, polyclonal antibodies (unconjugated), second antibodies (alkaline phosphatase conjugated), immunoglobulin screening and isotyping kits, protein A products and immunoassay reagents. Among the monoclonal antibodies are those approved for use in diagnostic kits, for example IgE, peroxidase-anti-peroxidase conjugated, human chorionic gonadotropin, T cell, ferritin conjugated, carcinogenic embryonic antigen (CEA), OKT-II, anti-rabies, human growth hormone, Total T4, prolactin, 125I-Ige, UCG, thyroid stimulating hormone, chlamydia, gentamicin and rubella. Other useful monoclonal antibodies include monoclonal antibodies for human cell surface antigens, monoclonal antibodies for murine cell surface antigens, monoclonal antibodies to complement and blood proteins, monoclonal antibodies to immunoglobulins (human), monoclonal antibodies to neurological antigens, monoclonal antibodies to tumor markers, monoclonal antibodies to cell components, Epstein Barr virus antigens, human lymphocyte antigen (HLA) typing, hematology antibodies, leucocyte antibodies, bacterial antigen, parasitic antigens, T-cell lymphotropic virus (HIV-III) and cyloskeletal antibodies. Useful polyclonal antibodies (unconjugated) include affinity purified antibodies to immunoglobulins, antibodies to plant viruses, antisera to human isoenzymes and chromatographically purified antibodies. Useful alkaline phosphatase conjugated second antibodies include affinity purified antibodies to immunoglobulins, antibodies to plant viruses, biotin-conjugated antibodies, fluorescein-isothiocyanate-conjugated antibodies (FITC), gold-conjugated antibodies, peroxidase-conjugated antibodies, rhodamine conjugated antibodies and iodine-conjugated antibodies. Polypeptide immunoassay reagents include EIA grade enzymes, enzyme-antibody complexes, reagents for immunology, enzyme linked immunosorbent assays (ELISA) for use as standards or controls, immunoelectrophoresis (IEP) assays, radioimmunoassays (RIA) for use as standards or controls, nephelometry for use as standards or controls, nuclear antigens and coatings for kit tubes and plate wells.

Other polypeptides contemplated by the present invention include polypeptides useful in cell biology/biochemistry, for example in serum-free cultures (as supplements and reagents for cell culture), in glycoprotein and carbohydrate research (endoglycosidoses, exoglycosidoses, enzymes for carbohydrate research, enzymes for analysis of glycoprotein oligosaccharides), as molecular weight markers (calibration proteins, e.g. for gel permeation chromatography, subunit proteins), proteases (for use in blood research, protein sequencing, tissue digestion and cell harvest, total digestion of proteins and immobilized proteases), cell surface recognition proteins (adenosine and analogs, cyclic nucleotides, phosphoinositides), phospholipases and bioluminescence assay reagents.

Yet other polypeptides contemplated for use herein are polypeptides of particular interest in the field of molecular biology, including various enzymes and reagents. The enzymes can include labelling enzymes, modifying enzymes, nucleases, polymerases, sequencing enzymes and restriction enzymes. The reagents can include inhibitors, antibiotics and miscellaneous other reagents.

Preferred polypeptides for use in accord with the instant invention include growth regulators. Among the preferred growth regulators are hematopoietic factors, which affect the maturation and proliferation of blood cells in lymphoid tissue and bone marrow; cytokines, which generally influence eukaryotic cell growth; and lymphokines, which affect lymphocyte growth. Specific polypeptides which are growth regulators or lymphokines are: interleukin 1, 2, 3 and 4; $\alpha$, $\beta$, and $\gamma$ interferons; granulocyte colony stimulating factor (G-CSF); granulocyte-macrophage CSF(GM-CSF); macrophage CSF(m-CSF); megakaryocyte CSF; multi CSF or IL-3 (also known as BPA, HCGF, MCGF and PSF); erythropoietin; lymphotoxin; tumor necrosis factor (TNF, also known as cachectin); $\alpha$ and $\beta$ transforming growth factor (TGF); platelet derived growth factor (PDGF); epidermal growth factor (EGF); nerve growth factor (NGF); insulin-like growth factor I and II (IGF I is also called somatomedin C); growth hormone (GF, also called somatotropin); and growth hormone releasing factor (GHRF, also called somatoliberin). See Clark et al, "The Human Hematopoietic Colony Stimulating Factors," *Science*, 1229–1237 (Jun. 5, 1987); Taniguchi, "Regulation of Cytokine Expression," *Ann. Rev. Imm.*, 6, 439–464 (1988); and Watson et al, *Molecular Biology of the Gene*, Vol. II, 4th Ed., Benjamin/Cummings Publishing (1987).

Other preferred polypeptides for use in accordance with this invention are fusion proteins. Fusion proteins are covalently linked proteins or portions of proteins. Thus, proteins or active fragments thereof having different purposes can be linked to provide a fused molecule having characteristics of both. Generally speaking, one of the proteins/protein fragments is a "seeker" and the other an "actor" or "destroyer". Illustrative such fusion proteins are pseudomonas exotoxin linked to IL-2, diphtheria toxin linked to IL-2 or either toxin linked to other proteins, or linkages between other proteins such as those preferred proteins described in the preceding paragraph, or portions thereof. See U.S. Pat. Nos. 4,545,985; 4,468,382; and 4,675,382; all of which are incorporated by reference herein in their entireties and relied upon.

Fusion proteins of IL-2 linked with toxin as described above are designed to kill cells with IL-2 receptors, thus find use in preventing graft-versus-host rejection. Other fusion proteins have varying utilities, depending on the proteins or portions thereof which are combined. Thus, for example, Substance P and a toxin form a fusion protein which can be used to relieve chronic pain, while $\alpha$-melanocyte-stimulating hormone (MSH) and diphtheria toxin form a fusion protein designed to kill melanoma cells.

Yet other preferred polypeptides for use herein are muteins, which are mutationally altered proteins. Preferred muteins are muteins of the preferred growth regulators and fusion proteins identified in the preceding paragraphs, and typically have the same purpose as the corresponding unaltered proteins. Especially preferred muteins include IL-2 muteins, described for example in U.S. Pat. Nos. 4,752,585 and 4,518,584, incorporated by reference herein in their entireties and relied upon; and muteins of $\beta$-interferon, described for example in U.S. Pat. Nos. 4,737,462 and 4,588,585, incorporated by reference herein in their entireties and relied upon.

The cyclodextrins contemplated for use herein are hydroxypropyl, hydroxyethyl, glucosyl, maltosyl and maltotriosyl derivatives of $\beta$-cyclodextrin and the corresponding derivatives of $\gamma$-cyclodextrin. The hydroxyalkyl groupings may contain one or more hydroxyl groups, e.g. hydroxypropyl (2-hydroxypropyl, 3-hydroxypropyl), dihydroxypropyl and the like. The glucosyl, maltosyl and maltotriosyl derivatives may contain one or more sugar residues, e.g. glucosyl or diglucosyl, maltosyl or dimaltosyl. Various mixtures of the cyclodextrin derivatives may be used as well, e.g. a mixture of maltosyl and dimaltosyl derivatives. Specific cyclodextrin derivatives for use herein include hydroxypropyl-$\beta$-cyclodextrin (HPCD or HPBCD), hydroxyethyl-$\beta$-cyclodextrin (HEBCD), hydroxypropyl-$\gamma$-cyclodextrin (HPGCD), hydroxyethyl-$\gamma$-cyclodextrin (HEGCD), dihydroxypropyl-$\beta$-cyclodextrin (2HPBCD), glucosyl-$\beta$-cyclodextrin ($G_1$-$\beta$-CD or $G_1$BCD), diglucosyl-$\beta$-cyclodextrin ($2G_1$-$\beta$-CD or $2G_1$BCD), maltosyl-$\beta$-cyclodextrin ($G_2$-$\beta$-CD or $G_2$BCD), maltosyl-$\gamma$-cyclodextrin ($G_2$-$\gamma$-CD or $G_2$GCD), maltotriosyl-$\beta$-cyclodextrin ($G_3$-$\beta$-CD or $G_3$BCD), maltotriosyl-$\gamma$-cyclodextrin ($G_3$-$\gamma$-CD or $G_3$GCD) and dimaltosyl-$\beta$-cyclodextrin ($2G_2$-$\beta$-CD or $2G_2$BCD), and mixtures thereof such as maltosyl-$\beta$-cyclodextrin/dimaltosyl-$\beta$-cyclodextrin.

Hydroxypropyl-$\beta$-cyclodextrin for use in the methods of the present invention is commercially available. Alternatively, it may be prepared by known methods, especially by use of the optimized procedure of Pitha et al,

*International Journal of Pharmaceutics*, 29, 73–82 (1986). The following is a typical procedure using the Pitha et al method:

31 g of sodium hydroxide were dissolved in 250 mL of water. Then, 100 g of β-cyclodextrin were added and the solvent was warmed to effect solution. The flask was cooled and 50 mL of propylene oxide were added. The flask was fitted with a dry ice/acetone condenser during the addition. The solution was allowed to come to room temperature and was stirred for 72 hours. The solution was then neutralized with concentrated hydrochloric acid and diluted with water. The solvent was removed in vacuo, leaving a syrup which was taken up in ethanol. After stirring for 30 minutes at room temperature, the sodium chloride produced was removed by filtration. The filter cake was washed with ethanol and the combined ethanol layers were reduced in vacuo. The residue was dissolved in water and dialyzed in cellulose acetate (#7, 38 mm, 4.6 mL/cm, molecular weight cut off=1000, Fisher Scientific). After 5 hours at 0° C., the solution was removed from the dialysis tubing and freeze-dried. The resulting solid was suspended in acetone and stirred overnight. The filtered solid was resuspended in acetone and stirred for 24 hours. The solid was collected by filtration and dissolved in 200 mL of water and then lyophilized. 75 grams of purified hydroxypropyl-β-cyclodextrin were obtained. The degree of substitution was calculated by NMR and by comparison with an authentic sample.

The Pitha et al method for preparation of HPBCD by condensation of propylene oxide with β-cyclodextrin in alkaline aqueous solution unfortunately suffers from disadvantages, particularly in purification of the product. After completion of the condensation, the reaction mixture is neutralized with hydrochloric acid, water is evaporated under vacuum and the syrupy residue is dissolved in ethanol to precipitate sodium chloride, the main by-product of the reaction. After filtration, ethanol is evaporated under vacuum and the residue is dissolved in water and dialyzed to remove the remaining sodium chloride and polymerization products of propylene oxide. During dialysis, part of the hydroxypropyl-β-cyclodextrin goes through the membrane and is lost. The dialysate is then freeze-dried, twice stirred in acetone and washed to remove the remaining polymerization products. Finally, hydroxypropyl-β-cyclodextrin is freeze-dried again. The second freeze-drying is necessary because the product after washing with acetone is not homogeneous.

To overcome these difficulties with the Pitha et al process, a new method has been developed by Maciej Smulkowski of the University of Florida, Gainesville, Fla. for the synthesis of HPBCD. This new method involves removal of sodium hydroxide from the reaction mixture by an ion exchange resin (H$^+$); as a result, several time-consuming steps of Pitha et al's purification can be avoided. Moreover, the amount of sodium hydroxide used by Pitha et al (7 equivalents for one of β-cyclodextrin) can be decreased to 2 equivalents of sodium hydroxide per cyclodextrin molecule, and still produce a product with the appropriate NMR and optical rotation.

According to the new method, β-cyclodextrin is first condensed with propylene oxide in alkaline solution, sodium hydroxide is removed on an ion exchange column (Dowex 50W-X8, H$^+$ form), the eluate is evaporated under vacuum to one-half of the original volume, the remaining solution is freeze-dried, the resulting white solid is washed with acetone and freeze-dried again, then subjected to grinding and sieving. Possible modifications of this method include: (1) use of the ionic exchange resin for neutralization in the reaction flask, with filtration of the resin and washing on the filter funnel; (2) use of calcium, magnesium, lithium or potassium hydroxide to dissolve the cyclodextrin; (3) removal of hydroxides after the reaction by saturating the reaction mixture with carbon dioxide or neutralization with sulfuric acid in place of the ion exchange resin; (4) use of even less sodium hydroxide (between 1 and 2 equivalents); and (5) elimination of the second freeze-drying.

The following is a typical procedure using the new, improved method:

50 g of β-cyclodextrin were dissolved in a solution of 3.53 g of sodium hydroxide in 75 mL of water and treated with 29 mL of propylene oxide at 0° C. The reaction mixture was maintained for 5 hours at that temperature, then was kept at room temperature for 42 hours. At the end of that time, the reaction mixture was passed through the Dowex 50W-X8 column (H$^+$ form), the column was washed with water and the eluate was evaporated under vacuum to a volume of 100 mL, then freeze-dried. The resulting white solid was washed with acetone to give 51 g of HPCD, with the same degree of substitution (4.7) and NMR as the HPCD prepared by the Pitha et al method. Residue on ignition was 0.0%. Optical rotation also was identical to that of the Pitha et al product.

Condensation of 25 g of β-cyclodextrin using 7.71 g of sodium hydroxide gave similar results.

A further improvement in the new, improved HPBCD synthesis utilizes activated carbon for purification of the solution prior to the last freeze-drying. Thus, when the aqueous solution from the Dowex 50 ionic exchange column was treated with activated carbon, most of the polymerization products were removed without loss of HPBCD, and the filtrate after only one washing with ethyl acetate was ready for final freeze-drying. In this way, only one freeze-drying was required. Crystallization of the final product instead of freeze-drying is also possible, at least on a small scale.

The product from the modified new process (using activated carbon) appears to be superior to that of the original new process and the Pitha et al process. First, the product is snow white and produces a colorless aqueous solution, whereas solutions of the earlier products were yellow. Secondly, the product is not oily, which may be due to removal of more highly substituted, less soluble, oily cyclodextrins.

HPBCD can be prepared in varying degrees of substitution, such as 5 or 7. Typically, the foregoing procedure is used to produce HPBCD (ASDS 7). The mass spectra for the isomeric mixture of HPBCD centers around 7 degrees of substitution. This spectra is obtained by "softly" ionizing the sample using fast atom bombardment. The generated spectra is similar to those previously reported (obtained by Californium-252 plasma desorption) in both the symmetry of the isomeric distribution and the numerical spread of the isomers formed.

Hydroxyethyl-β-cyclodextrin (HEBCD) can be prepared analogously to HPBCD, utilizing the improved procedure detailed above but substituting an equivalent quantity of ethylene oxide for the propylene oxide there employed.

The synthesis of 2-hydroxypropyl-γ-cyclodextrin (HPGCD) similarly uses the same basic procedure as for HPBCD, substituting γ-cyclodextrin for the β-cyclodextrin starting material. However, because γ-cyclodextrin contains eight glucose residues compared to seven for β-cyclodextrin, the amount of propylene oxide used can be reduced in order to lower the degree of substitution. Use of 0.75 mole of propylene oxide per 0.077 mole of γ-cyclodextrin (~20% excess considering 8 OH groups)

affords HPGCD with a degree of substitution of 8, while use of 0.56 mole of propylene oxide (~10% less than equivalent) gives a degree of substitution of about 7.

Hydroxyethyl-γ-cyclodextrin (HEGCD) can be prepared similarly to HPGCD as described in the preceding paragraph, simply using an equivalent quantity of ethylene oxide in place of the propylene oxide.

Thus, the hydroxyalkyl cyclodextrins intended for use herein can be prepared by procedures described by Pitha et al or variations thereof. Obtained by these procedures, the cyclodextrins are intrinsically amorphous mixtures. The importance of the amorphous nature of the cyclodextrins is described by Pitha et al, *J. Pharm. Sci.*, Vol. 74, No. 9, 987–990 (September 1985) and in Pitha U.S. Pat. No. 4,727,064. The advantages of the amorphous nature of these materials are more pronounced at higher concentrations of cyclodextrin.

For use with polypeptides, it is highly desirable to use cyclodextrin which is relatively free of impurities, i.e. oxidizing agents, peroxides, propylene oxide or other chemicals used to prepare the cyclodextrins, because oxidation can render the polypeptide less effective. Preferably, the impurity level will be below 100 μM peroxide or its equivalent.

The other cyclodextrins intended for use in the present invention, i.e. the glucosyl, maltosyl and maltotriosyl derivatives of β- and γ-cyclodextrin, are branched cyclodextrins which are highly soluble in water as compared to the parent cyclodextrins. These branched cyclodextrins can be produced by microbiological processes from the parent cyclodextrins. Glucosyl-β-cyclodextrins can be obtained from the mother liquor of a large-scale β-cyclodextrin synthesis with *Bacillus ohbensis* cyclomaltodextrin glucanotransferase; see Koizumi et al, *Chem. Pharm. Bull.*, 35 (8), 3413–3418 (1987) and reference cited therein. Maltosyl and maltotriosyl β- and γ-cyclodextrins can be prepared from the parent cyclodextrin and maltose or maltotriose through the reverse action of Pseudomonas isoamylase or Klebsiella aerogenes pullulanase, while glucosyl-γ-cyclodextrin can be prepared by enzymatic hydrolysis of maltosyl-γ-cyclodextrin; see Okada et al, *Chem. Pharm. Bull.*, 36 (6), 2176–2185 (1988) and references cited therein. The preparation of maltosyl-β-cyclodextrin by reacting maltose with β-cyclodextrin in the presence of pullulanase is also described in Japanese Kokai 61-287902, published Dec. 18, 1986, and Japanese Kokai 61-197602, published Sep. 1, 1986. A mixture of maltosyl-β-cyclodextrin and various dimaltosyl-β-cyclodextrins may be conveniently employed. See also Kainuma et al U.S. Pat. No. 4,668,626, issued May 26, 1987.

Polypeptides such as proteins present unique solubility and stability problems as compared to other drug molecules. These are a reflection of the unique structure of the polypeptides. Proteins, for example, are very large molecules of high molecular weight having numerous hydrophobic and hydrophilic regions within a single molecule. Moreover, the three-dimensional structure or conformation of proteins is critical to their activity and can be easily affected detrimentally by the protein's environment, an unfavorable environment leading to aggregation. Thus, the solubilization and stabilization of these, complex molecules is difficult to accomplish and the ability of an untried agent to achieve solubilization/stabilization, and to do so without appreciable loss of activity, cannot be readily predicted. However, the present inventors have determined that a selected group of cyclodextrins, i.e. the hydroxypropyl, hydroxyethyl, glucosyl, maltosyl and maitotriosyl derivatives of β- and -γ-cyclodextrin (the hydroxypropyl and hydroxyethyl derivatives being preferably prepared in amorphous form as described hereinabove) are well-suited for use in solubilizing/stabilizing the polypeptides defined hereinabove, especially the proteins. The following examples illustrate the solubilization/stabilization results which can be achieved in accord with the present invention. These examples are not intended to limit the invention in any manner whatsoever.

EXAMPLE 1

Preliminary Testing

Preliminary studies on the use of a representative cyclodextrin encompassed by the present invention, i.e. hydroxypropyl-β-cyclodextrin (HPBCD), as a stabilizer for interleukin-2 (IL-2) were conducted by first assessing whether a HPBCD-formulated solution of IL-2 could be lyophilized to produce a clear solution upon reconstitution. This has proved to be a good first test for IL-2 formulation screening because very few agents give a clear IL-2 solution after lyophilization and reconstitution.

First, IL-2 was formulated with HPBCD such that the final concentrations of 25.0 and 12.5 per cent HPBCD were present in 1 mL of a 1 mg/mL IL-2 solution. These were lyophilized in an LSL Lyolab lyophilizer using the following cycle: primary drying at –30° C. for 18 hours, temperature ramped up to 15° C. at a rate of 12°/minute, followed by secondary drying at 15° C. for 20 hours, all steps being carried out under a vacuum of 50 microns. The lyophilized preparations were reconstituted with 1 mL of water for injection (WFI). On visual observation, the solutions were found to be clear. Additionally, they gave light scattering numbers of 61 and 66 when analyzed by a light scattering assay for assessing clarity of solutions. This assay determines the light scattering value by using a fluorimeter to measure the amount of light (510 nm) scattered from a sample at 90 degrees. Usually, a value of 500 or below represents a good and clear solution, a value in the range 500–1000 represents a marginal solution, and scattering values >1000 are obtained from turbid and hence unacceptable solutions.

Next, to determine the minimum HPBCD level needed to give a clear solution upon reconstitution, a range of concentrations of HPBCD (0.5–25% w/v) were formulated with IL-2 (1 mg), 1 or 2% sucrose, and 10 mM citrate buffer in a total volume of 1 mL per vial (the excipient). These were lyophilized as before, and reconstituted with 1 mL, of WFI. A light scattering assay was used to measure the clarity of the resultant solution. As shown in FIG. 1 by the very low fluorimeter values (30–60), a clear solution of IL-2 was obtained from all samples across the tested range. Moreover, Western blot analysis of the samples used for the light scattering analysis showed no appreciable increase in dimers when IL-2 was lyophilized with HPBCD.

EXAMPLE 2

Further Light Scattering Testing

Figure 2:
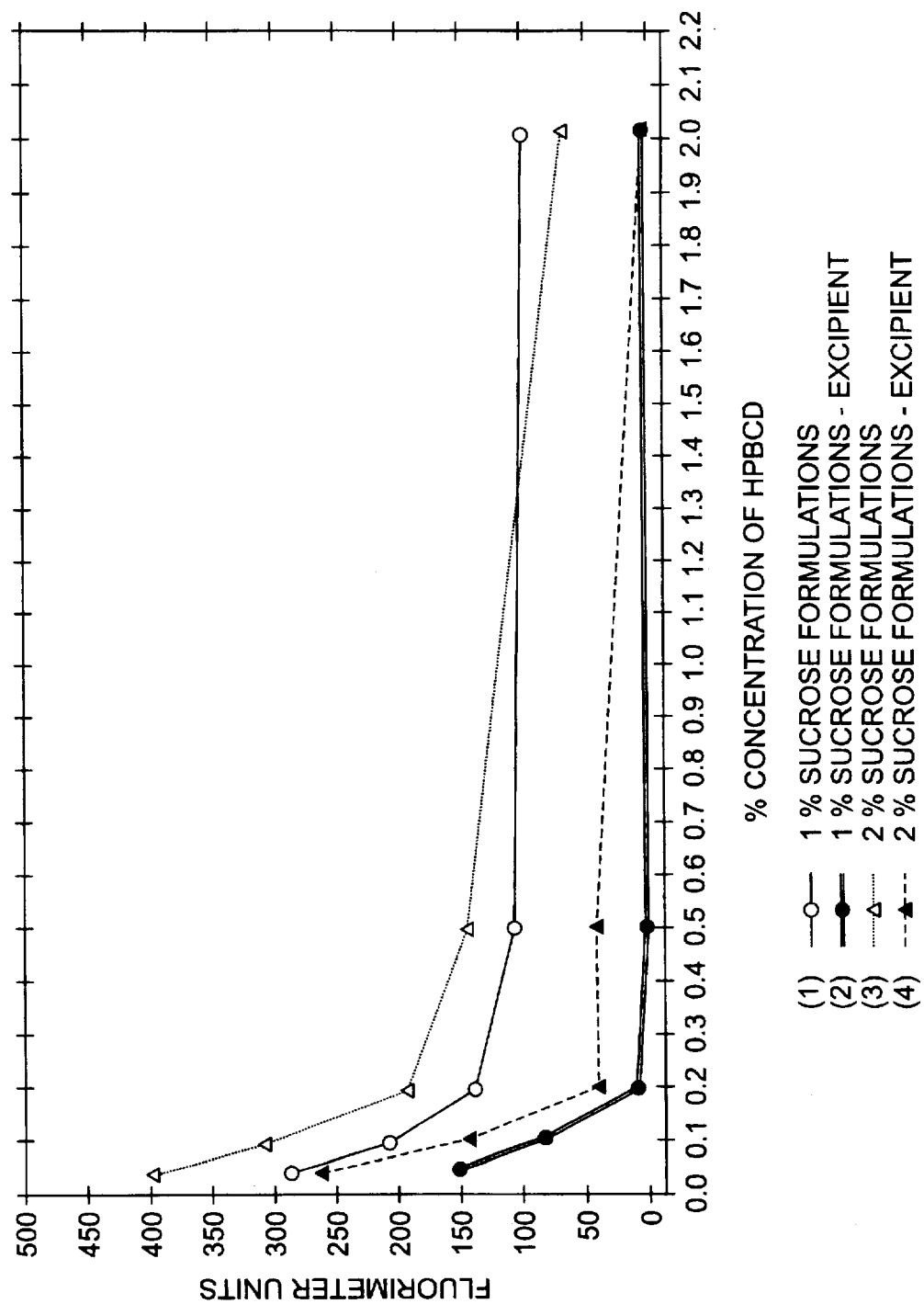
FIG. 2 is a plot of fluorimeter units as an indication of initial light scattering for samples of HPBCD formulations of IL-2 (1 mg/mL) with sucrose bulking.

All IL-2 formulations were lyophilized in the usual manner as described above. The lyophilized plugs were reconstituted with water and characterized as follows:

Following the experiments detailed in Example 1, lower concentrations of HPBCD were tested in an attempt to determine the minimum level of the excipient needed to stabilize a 1 mg/mL IL-2 formulation. Also, samples were bulked with sucrose to obtain more homogeneous plugs. Light scattering values were obtained as in Example 1. The results are depicted in FIG. 2. Curves 1 and 3 in the figure represent the light scattering values for formulation samples without correction for excipient scattering, while curves 2 and 4 show these values after excipient scattering corrections (obtained by subtracting the values for the control formulation without IL-2). An increase in scattering values, indicating a decrease in the clarity of the solution, is seen when the concentration of HPBCD in the formulation dropped below 0.2%. On a molecular level, this translates to a minimum of 20 molecules of HPBCD per molecule of IL-2. See Table 1 below.

TABLE 1

MOLAR RATIOS OF HPBCD AND IL-2 IN SELECTED FORMULATIONS (1,2)

| % HPBCD in formulation | Mole HPBCD/Mole IL-2 |
|---|---|
| 0.05 | 4.87 |
| 0.10 | 9.74 |
| 0.20 | 19.47 |
| 0.50 | 48.68 |
| 2.00 | 194.72 |

1. These values have been calculated from a HPBCD molecular weight of 1540, assuming the average degree of β-cyclodextrin substitution to be ~7.
2. IL-2 concentration is 1 mg/mL in the formulations.

EXAMPLE 3

Ultracentrifugation Assay

Figure 3:
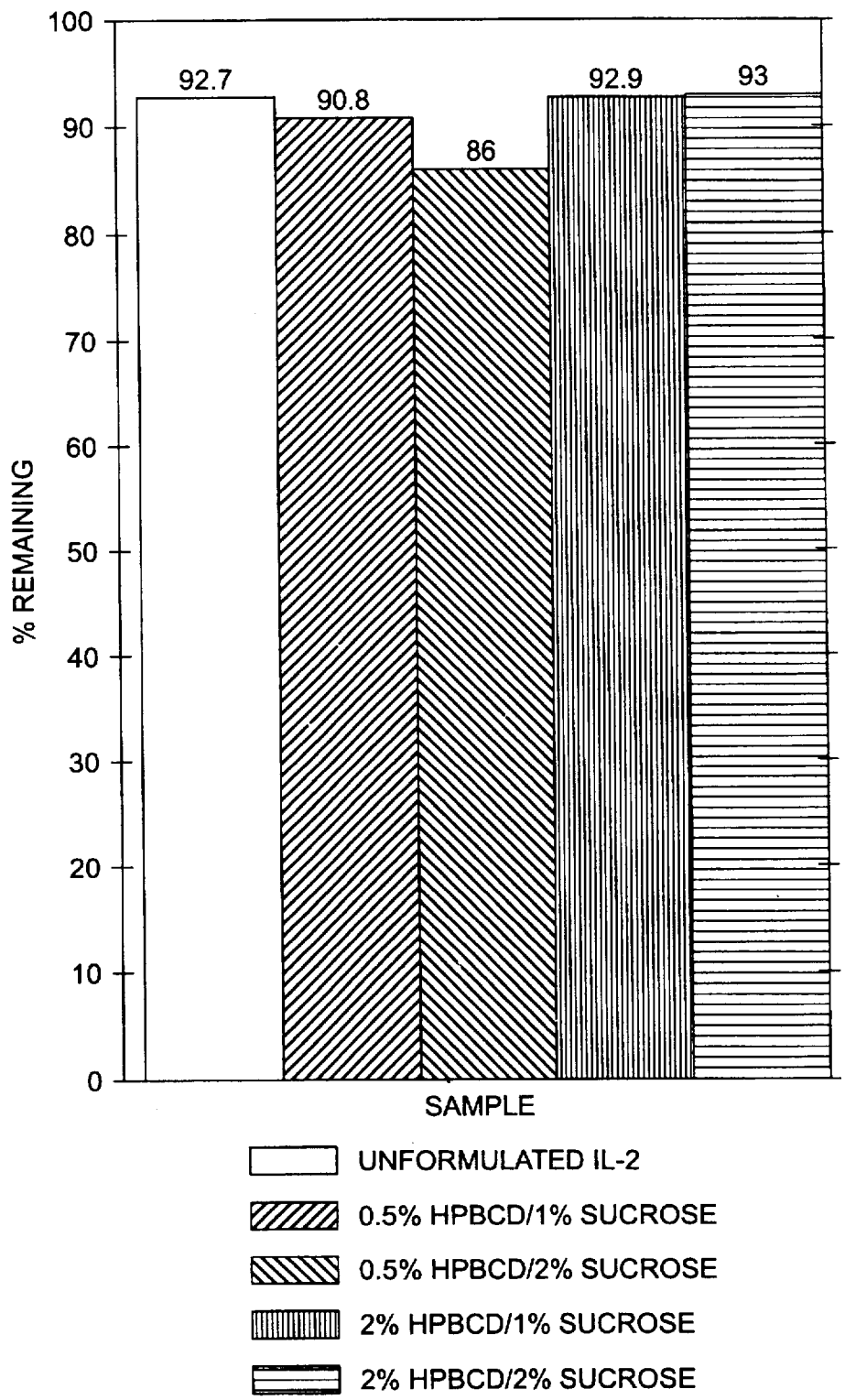
FIG. 3 is a bar graph depicting the results of an ultracentrifugation assay of samples of IL-2 formulated with HPBCD as compared to unformulated IL-2.

Ultracentrifugation is a simple method of detecting the presence of high molecular weight aggregates and oligomers. Ultracentrifugation was performed in a Beckman L8-70 using a type 70.1 Ti rotor. Five milliliters of the sample formulation were spun at 105,000×g for 1 hour. The supernatant was measured by absorbance at 280 nm. Said absorbance was then compared to that prior to centrifugation. Reconstituted samples of IL-2 formulated with HPBCD were tested by this assay. Samples were prepared similarly to those in Example 2 and the results are presented in FIG. 3. As seen in the figure, unformulated IL-2, before lyophilization, contains ~93% of the protein in the supernatant by this assay, indicating that IL-2 is nearly completely unaggregated in solution. IL-2 formulated with 0.5 or 2.0 per cent HPBCD with 1% or 2% sucrose behaved similarly to the unformulated IL-2. These data indicate that the protein was present in an unaggregated form when the HPBCD formulations were reconstituted.

EXAMPLE 4

Bioactivity Assay

Figure 4:
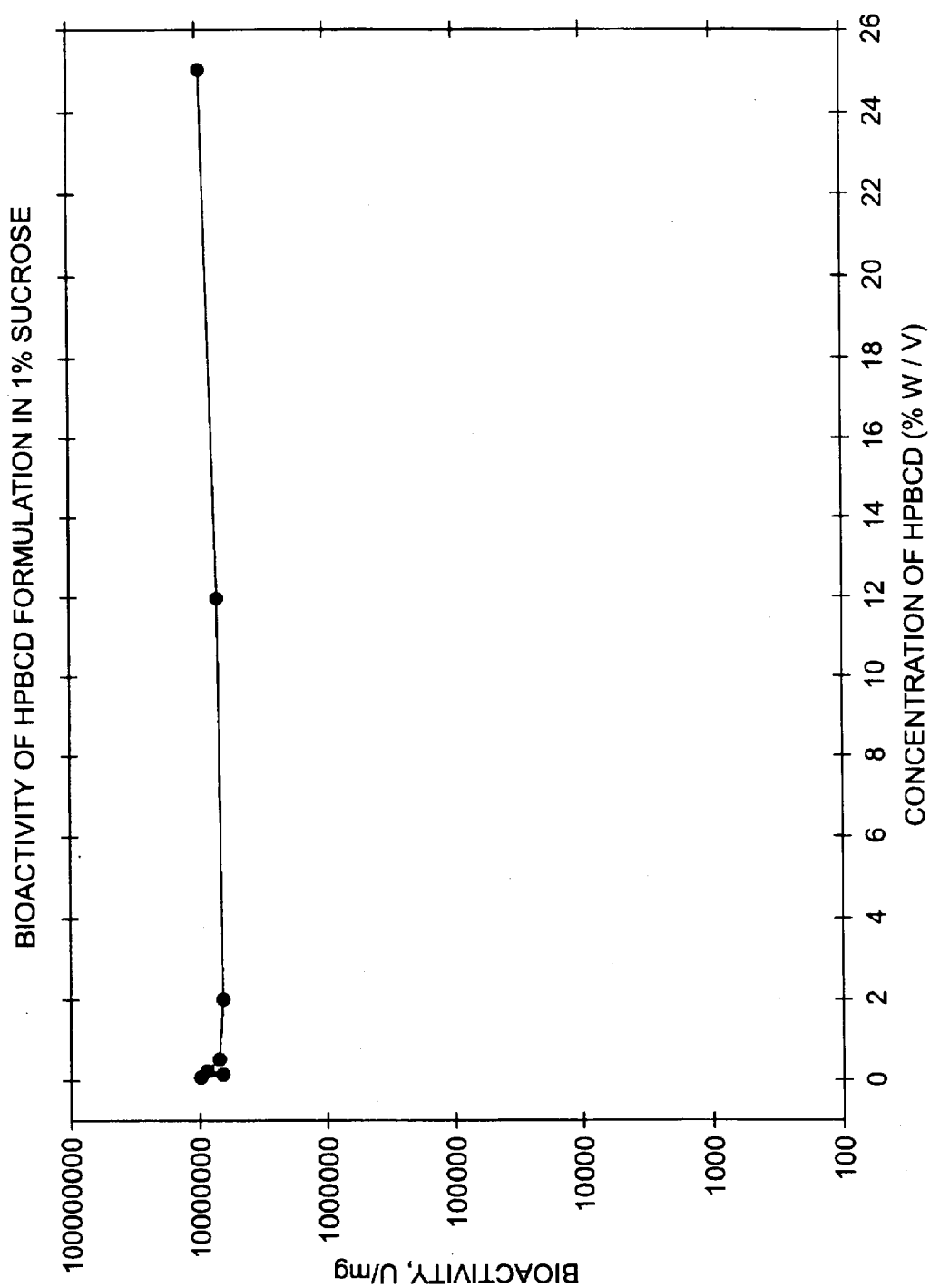
FIG. 4 is a semi-logarithmic plot depicting the biological activity of samples of IL-2 containing increasing concentrations of HPBCD.

Formulations of IL-2 containing 0.05 to 25.00% HPBCD were lyophilized and then reconstituted as described in Example 2. Bioactivity of IL-2 samples was measured by a HT-2 Cell Proliferation assay using the MTT stain. This assay has been adapted from the IL-2 assay described by Gillis et al (1978) in *Journal of Immunology* (Volume 120), pages 2027–2032. As seen from FIG. 4, IL-2 remained fully biologically active when formulated with HPBCD.

Western Blot Analysis

To assess protein purity, Western blots were run on a number of IL-2 formulations which were combined with various concentrations of HPBCD, lyophilized and then reconstituted with water as described before. Samples tested included the following HPBCD formulations of IL-2: 0.05% HPBCD with 1% sucrose, 0.1% HPBCD with 1% sucrose, 0.2% HPBCD with 1% sucrose, 0.5% HPBCD with 1% sucrose, 2.0% HPBCD with 1% sucrose, 1% β-cyclodextrin with 1% sucrose, 0.5% HPBCD with 2% sucrose and 2.0% HPBCD with 2% sucrose. Unformulated IL-2 was also tested. The HPBCD and β-cyclodextrin formulations were tested after 1 week at 37 C. There was a slight amount of dimer in the HPBCD formulations after lyophilization and subsequent rehydration, similar to the amounts seen in unformulated IL-2, but the results for the HPBCD formulations indicated above were all considered to be excellent. IL-2 formulated with unmodified β-cyclodextrin, which gave a somewhat clear solution after reconstitution of the lyophilized plug (scattering number ~300), exhibited a darker dimer band in the Western than the HPBCD formulations.

EXAMPLE 5

HPBCD was formulated with selected polypeptides as described previously (IL-2, tumor necrosis factor or TNF, macrophage colony stimulating factor or m-CSF, insulin and human growth hormone) and the formulations were stored under various conditions of time and temperature. Light scattering values (determined as described before) and visual appearance were noted for each formulation. The results are tabulated below:

TABLE 2

PART A
CLARITY OF HPBCD/PROTEIN FORMULATIONS

| Protein | Formulation | Storage Time | Temp | Type | Light Scattering** | Visual Appearance |
|---|---|---|---|---|---|---|
| IL-2 | 1.0 mg/mL 10 mM Na citrate, pH 6.5 2.0% HPBCD, 2.0% sucrose | 4 weeks | 4° C. | lyophilized | 66 | clear |
| | same | 4 weeks | 37° C. | lyophilized | 90 | clear |
| | same | 4 weeks | 25° C. | liquid | 26 | clear |
| | same | 4 weeks | 37° C. | liquid | 402 | particulates |
| TNF | 0.25 mg/mL 10 mM Na citrate, pH 6.5 0.5% HPBCD, 1.0% sucrose | 4 weeks | 4° C. | lyophilized | 96 | clear |
| | same | 4 weeks | 37° C. | lyophilized | 88 | clear |
| m-CSF | 1.0 mg/mL 10 mM Na citrate, pH 6.5 2.0% HPBCD, 2.0% sucrose | 4 weeks | 4° C. | lyophilized | 34 | clear |
| Insulin | 1.0 mg/mL | 4 weeks | 4° C. | lyophilized | 26 | clear |

TABLE 2-continued

PART A
CLARITY OF HPBCD/PROTEIN FORMULATIONS

| Protein | Formulation | Storage Time | Storage Temp | Storage Type | Light Scattering** | Visual Appearance |
|---|---|---|---|---|---|---|
| (Bovine pancreatic, Sigma) | 10 mM Na citrate, pH 6.5 0.15N HCl 0.63% L-arginine HCl 1.0% HPBCD, 1.0% sucrose | | | | | |
| Human Growth Hormone (Sigma) | 1.0 mg/mL 10 mM Na citrate 3.0% HPBCD, 2.0% sucrose 1.7% Mannitol | 4 weeks | 4° C. | lyophilized | 490* | slightly hazy* |

*Human Growth Hormone, from Sigma, was obtained as a lyophilized product which reconstituted as a hazy solution. Formulating HGH with 3% HPBCD reduced the haziness.
**Without correction for the excipient control.

TABLE 2

PART B
CLARITY OF PROTEIN FORMULATIONS WITHOUT STABILIZER

| Protein | Formulation | Type | Light Scattering | Visual Appearance |
|---|---|---|---|---|
| IL-2 | 1.0 mg/mL 10 mM Na citrate, pH 6.5 | lyophilized | 558 | suspended particulates |
| | same | liquid | 26 | particulates begin to appear on storage at room temperature after 2 hours |
| TNF* | 0.25 mg/mL 10 mM Na citrate, pH 6.5 | lyophilized | 26 | clear |
| m-CSF | 1.0 mg/mL 10 mM Na citrate, pH 6.5 | lyophilized | 46 | clear |
| Insulin (Bovine pancreatic, Sigma) | 1.0 mg/mL 10 mM Na citrate, pH 6.5 | lyophilized | — | lyophilized plug does not dissolve |

*Although TNF solution was clear upon reconstitution, the solution formed 3–5% dimer in 4 weeks at 37° C., whereas with TNF formulated with HPBCD, no appreciable dimer (<0.2%) formed in the same time.

Bioactivity of selected samples was measured by known procedures. IL-2 bioactivity was determined as described before. TNF activity was measured using an in vitro cell cytotoxicity assay utilizing a TNF sensitive mouse L-929 fibroblast target cell line. This assay has been adapted from techniques discussed by J. M. Ostrove and G. E. Gifford in *Proc. Soc. Exp. Biol. Med.* 160:354–358 (1979) and M. R. Ruff and G. E. Gifford in *Inf. Immun.* 31:380–385 (1981). The m-CSF bioassay was performed by using an NFS-60 murine retrovirus-induced myeloid leukemia cell line. The pertinent references for the CSF assay are: J. Ihle et al., *Advances in Oncology*, Vol. 4, pp. 95–137, G. Klein ed. (Raven Press, NY) and J. C. Lee et al., *J. Immunol.* 128:2393–2398 (1982).

TABLE 3

BIOACTIVITY OF HPBCD/PROTEIN FORMULATIONS

| PROTEIN | SPECIFIC ACTIVITY BEFORE FORMULATION U/MG | FORMULATION | SPECIFIC ACTIVITY IN FORMULATION U/MG |
|---|---|---|---|
| IL-2 | $14 \times 10^6$ | IL-2 1 mg/mL HPBCD 2% Sucrose 2% 10 mM Citrate pH 6.5 | $8.93 \times 10^6$ |
| TNF | $15.6 \times 10^6$ | TNF 0.25 mg/mL HPBCD 0.5% Sucrose 1% 10 mM Citrate pH 6.5 | $26.5 \times 10^6$ |
| m-CSF | $8.9 \times 10^7$ | m-CSF 1 mg/mL HPBCD 2% Sucrose 2% 10 mM Citrate pH 6.5 | $4.93 \times 10^7$ |

The data for the HPBCD/protein formulations are similar to the values for unformulated IL-2, TNF and m-CSF, indicating that these proteins retain their full biological activity after formulation with HPBCD.

Selected samples formulated as specified in TABLE 2 were also assessed for dimer formation as an indication of protein denaturation. SDS-PAGE gels were silver stained to enhance detail for the detection of dimer in very small quantities. Normal Comassie or Fast Green stains do not normally show dimer formation at these low levels. There was no substantial dimer formation in IL-2 after 12 weeks at 4° C., in TNF after 10 weeks at 4° C. and in human growth hormone after 7 weeks at 4° C. m-CSF showed essentially the same composition on SDS-PAGE after 7 weeks of storage at 4° C. as it displayed at the beginning of the study. m-CSF exists as a dimer in solution and hence runs as a dimer. Therefore, these results represent no change in the nature of the protein after formulation with HPBCD. Insulin exhibited slight dimer formation but the amount was still very small.

EXAMPLE 6

Fourth derivative ultraviolet spectroscopy (4D-UV) is a technique which can assess environmental changes of the aromatic amino acids, thus denoting possible conformational changes. No difference in the fourth derivative spectrum of the protein was noted for IL-2 formulated with HPBCD as compared with unformulated IL-2, 1 mg/mL. The HPBCD formulations contained:

| IL-2 | HPBCD | Sucrose | Buffer |
|---|---|---|---|
| 1 mg/mL | 0.2% | 0.5% | 10 mM citrate pH 6.5 |
| 1 mg/mL | 0.5% | 0.5% | 10 mM citrate pH 6.5 |
| 1 mg/mL | 2.0% | 2.0% | 10 mM citrate pH 6.5 |

The formulation of protein and cyclodextrin in accord with the present invention may be carried out as a separate operation utilizing purified protein as the starting material, or the formulation with cyclodextrin may be incorporated into purification of the protein. By way of example, there is described below a formulation of a selected peptide, IL-2, with a selected cyclodextrin, HPBCD, which is carried out during the purification process:

Thus, the protein starting material may be recombinant IL-2 present in the product in a gel filtration pool which is frequently the final step of protein purification. A concentrated HPBCD solution may be added at this point in an appropriate amount to form a complex with IL-2 and stabilize it in solution. The concentrations of HPBCD and IL-2 are adjusted, if desired, and typically a bulking agent is added. The bulking agent is present in the solution at a level of about 0.5 to 10% by weight, preferably 1 to 5% by weight. Preferred bulking agents are water-soluble, stable and do not react with IL-2, for example sucrose, lactose, trehalose, maltose, mannitol, sorbitol, starches, starch hydrolysates, microcrystalline celluloses and albumin such as human serum albumin. The bulking agent protects the protein during lyophilization, gives a more homogeneous lyophilized product and also makes the freeze-dried product, when placed in unit dosage containers, easily seen by the naked eye.

After adding the bulking agent, the unit dosage amounts (i.e. volumes that will provide about 0.01 to 2 mg, preferably 0.2 to 1.0 mg, IL-2 per dose) of the solution are dispensed into containers, the containers are capped with a slotted stopper, and the contents are lyophilized using conventional freeze-drying conditions and apparatus.

The lyophilized, sterile product may consist of a mixture of (1) recombinant IL-2, (2) bulking agent (e.g. sucrose), (3) HPBCD and (4) a small amount of buffer that will provide a near physiological pH when the mixture is reconstituted. The recombinant IL-2 will typically constitute about 0.015% to 3.85% by weight of the mixture, more preferably about 0.4% to 2.0% of the mixture. HPBCD will typically constitute about 0.2% to 10% by weight of the mixture.

The lyophilized mixture may be reconstituted by injecting a conventional parenteral aqueous injection liquid such as water for injection, Ringer's injection, dextrose injection, dextrose and salt injection, or the like, or aqueous HPBCD solution into the vial. The amount of injection liquid added to the vial will typically be in the range of 1 to 10 mL, preferably 1 to 2 mL for intramuscular or subcutaneous injections, with larger volumes usable for intravenous injections.

The reconstituted formulation is suitable for parenteral administration to humans or other mammals to provide IL-2 therapy thereto. Such therapy is appropriate for a variety of immunomodulatory indications such as T cell mutagenesis, induction of cytotoxic T cells, augmentation of natural killer cell activity, induction of IFN-gamma, restoration or enhancement of cellular immunity (e.g., treatment of immune deficient conditions) and augmentation of cell mediated anti-tumor activity.

Generally speaking, when formulation with cyclodextrin occurs as part of the polypeptide purification process, the cyclodextrin will be introduced as an aqueous solution comprising at least 0.01% (w/v) cyclodextrin (e.g. HPBCD), more preferably from about 0.1% (w/v) to about 60% (w/v) cyclodextrin (e.g. HPBCD). Most preferably, and especially when the polypeptide is IL-2, the range is from about 0.2% (w/v) to about 60% (w/v) cyclodextrin.

When an already purified polypeptide is to be formulated in accord with the present invention, the polypeptide (typically lyophilized) may be simply dissolved by mixing with an aqueous cyclodextrin (e.g. HPBCD) solution of the selected concentration, the aqueous cyclodextrin solution generally comprising at least 0.01% (w/v) cyclodextrin, e.g. HPBCD, more preferably from about 0.1% (w/v) to about 60% (w/v) cyclodextrin, e.g. HPBCD. Most preferably, the range is from 0.2% (w/v) to about 60% (w/v) cyclodextrin, particularly when IL-2 is the polypeptide. The amount of cyclodextrin (e.g. HPBCD) used will vary with the particular polypeptide selected, but will in any event be an effective stabilizing and/or solubilizing amount. A formulation prepared in this manner could be administered in this form, or lyophilized and subsequently reconstituted. In a lyophilized composition, the weight ratio of cyclodextrin to polypeptide will generally be between about 1:1 to 200:1, preferably between about 2:1 to 50:1.

As an alternative to the above, in selected situations the already purified polypeptide may be in liquid form (already dissolved in an appropriate aqueous medium) and the selected cyclodextrin may be added in dry form in a sufficient stabilizing amount.

The drug formulations prepared in accord with the present invention can be used to treat a variety of conditions, depending upon the pharmacological nature of the polypeptide selected for administration.

Preferably, the parenteral drug formulations prepared in accordance with the present invention comprise the selected polypeptide and an effective solubilizing and/or stabilizing amount of the selected cyclodextrin in an aqueous media. Preferably, the formulations are substantially free of organic solvent, are sterile and pyrogen-free, and are prepared in accord with accepted pharmaceutical procedures, for example as described in Remington's Pharmaceutical Sciences, seventeenth edition, ed. Alfonso R. Gennaro, Mack Publishing Company, Easton, Pa. (1985), 1518–1552. The aqueous sterile injection solutions may further contain antioxidants, buffers, bacteriostats, isotonicity adjusters and like additions acceptable for parenteral formulations. Various unit dose and multi-dose containers, e.g. sealed ampules and vials, may be used, as is well-known in the art. The essential ingredients of the sterile parenteral formulations, i.e. the selected polypeptide, water and selected cyclodextrin, may be presented in a variety of ways, just so long as the solution ultimately administered to the patient contains the appropriate amounts of the essential ingredients. Thus, for example, the polypeptide/cyclodextrin/water formulation may be presented in a unit dose or multi-dose container, ready for injection. As another example, a concentrated solution of polypeptide/cyclodextrin/water may be presented in a separate container from a diluting liquid (water or cyclodextrin/water) designed so that the contents can be combined to give a formulation containing appropriate amounts for injection. As another alternative, the polypeptide or, preferably, a polypeptide/cyclodextrin combination may be provided in a freeze-dried condition in one container, while a separate container contains diluting liquid (water or cyclodextrin/water, depending on the amount of cyclodextrin in the other container), again designed so that the contents can be combined to give a formulation containing the appropriate amounts of the essential ingredients. In any event, the contents of each container will be sterile.

In general terms, the therapeutic dosage ranges for administration of polypeptides in the parenteral formulations described herein will be the same as those characteristically used for parenteral administration of the polypeptide. Naturally, such therapeutic dosage ranges will vary with the size and species of the patient, the condition for which the formulation is administered, the type of parenteral administration employed and the like. The quantity of given dosage form needed to deliver the desired dose of active ingredient will of course depend upon the concentration of the peptide in the parenteral formulation.

While many polypeptides are administered by injection, some may be given orally. These could be stabilized with the selected cyclodextrin in accord with this invention, then formulated as tablets, capsules or the like in the usual manner, with well-known carrier materials. See *Remington's Pharmaceutical Sciences*, referred to hereinabove.

Diagnostics for in vivo use formulated according to this invention will be prepared in the same manner as the therapeutics described above, except that the unit dosage forms will contain a diagnostically effective amount rather than a therapeutically effective amount of the selected polypeptide. On the other hand, in vitro diagnostics need not be pharmaceutically acceptable. Thus, in vitro diagnostic components can, for example, be protected from exogenous contamination by the addition of bacteriostatic or fungistatic agents which are prohibited for in vivo applications. Other ingredients in the in vitro diagnostics, e.g. chromogens, likewise need not meet the requirements for materials present in pharmaceutical formulations.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims.

What is claimed is:

1. A method for stabilizing a protein in need of stabilization against denaturation or aggregation, said method comprising combining said protein with an effective stabilizing amount of cyclodextrin selected from the group consisting of hydroxypropyl, hydroxyethyl, glucosyl, maltosyl and maltotriosyl derivatives of β- and γ-cyclodextrin, said stabilizing amount of cyclodextrin being sufficient to prevent denaturation or aggregation of said protein, said protein being other than an interleukin.

2. A method according to claim 1, wherein said cyclodextrin is in an aqueous solution.

3. A method according to claim 2, wherein said aqueous solution comprises at least 0.1% (w/v) of cyclodextrin.

4. A method according to claim 3, wherein said aqueous solution comprises from about 0.2% (w/v) to about 60% (w/v) of cyclodextrin.

5. A method according to claim 1, wherein said cyclodextrin is hydroxypropyl-β-cyclodextrin.

6. A method according to claim 5, wherein said hydroxypropyl-β-cyclodextrin is in an aqueous solution.

7. A method according to claim 6, wherein said aqueous solution comprises at least 0.1% (w/v) of hydroxypropyl-β-cyclodextrin.

8. A method according to claim 7, wherein said aqueous solution comprises from about 0.2% (w/v) to about 60% (w/v) of hydroxypropyl-β-cyclodextrin.

9. A method according to claim 2, wherein said protein is superoxide dismutase.

10. A method according to claim 2, wherein said protein is insulin.

11. A method according to claim 2, wherein said protein is tissue plasminogen activator.

12. A method according to claim 2, wherein said protein is erythropoietin.

13. A method according to claim 2, wherein said protein is an interferon.

14. A method according to claim 13, wherein said interferon is β-interferon.

15. A method according to claim 2, wherein said protein is a growth hormone.

16. A method according to claim 2, wherein said protein is epidermal growth factor.

17. A method according to claim 2, wherein said protein is tumor necrosis factor.

18. A method according to claim 2, wherein said protein is atrial natriuretic factor.

19. A method according to claim 2, wherein said protein is a colony stimulating factor.

20. A method according to claim 2, further comprising lyophilizing the aqueous solution containing said protein and said cyclodextrin.

21. A composition comprising a protein in need of stabilization against denaturation or aggregation and an effective stabilizing amount of cyclodextrin selected from the group consisting of hydroxypropyl, hydroxyethyl, glucosyl, maltosyl and maltotriosyl derivatives of β- and γ-cyclodextrin, said stabilizing amount of cyclodextrin being sufficient to prevent denaturation or aggregation of said protein, said protein being other than an interleukin.

22. An aqueous composition according to claim 21.

23. A composition according to claim 22, comprising least 0.1% (w/v) of cyclodextrin.

24. A composition according to claim 23, comprising from about 0.2% (w/v) to about 60% (w/v) of cyclodextrin.

25. A composition according to claim 22 wherein said cyclodextrin is hydroxypropyl-β-cyclodextrin.

26. A composition according to claim 25, comprising at least 0.1% (w/v) of hydroxypropyl-β-cyclodextrin.

27. A composition according to claim 26, comprising from about 0.2% (w/v) to about 60% (w/v) of hydroxypropyl-β-cyclodextrin.

28. A composition according to claim 22, wherein said protein is superoxide dismutase.

29. A composition according to claim 22, wherein said protein is insulin.

30. A composition according to claim 22, wherein said protein is tissue plasminogen activator.

31. A composition according to claim 22, wherein said protein is erythropoietin.

32. A composition according to claim 22, wherein said protein is an interferon.

33. A composition according to claim 32, wherein said interferon is β-interferon.

34. A composition according to claim 22, wherein said protein is a growth hormone.

35. A composition according to claim 22, wherein said protein is epidermal growth factor.

36. A composition according to claim 22, wherein said protein is tumor necrosis factor.

37. A composition according to claim 22, wherein said protein is atrial natriuretic factor.

38. A composition according to claim 22, wherein said protein is a colony stimulating factor.

39. A composition according to claim 22, suitable for human or veterinary administration.

40. A composition according to claim 22, suitable for in vitro use.

41. A lyophilized composition comprising a protein in need of stabilization against denaturation or aggregation and an effective stabilizing amount of cyclodextrin selected from the group consisting of hydroxypropyl, hydroxyethyl, glucosyl, maltosyl and maltotriosyl derivatives of β- and γ-cyclodextrin, said stabilizing amount of cyclodextrin being sufficient to prevent denaturation or aggregation of said protein, said protein being other than an interleukin.

42. A composition according to claim 41, comprising a cyclodextrin to protein weight ratio of from about 1:1 to about 200:1.

43. A composition according to claim 42, comprising a cyclodextrin to protein weight ratio of from about 2:1 to about 50:1.

44. A composition according to claim 41, wherein said cyclodextrin is hydroxypropyl-β-cyclodextrin.

45. A composition according to claim 44, comprising a cyclodextrin to protein weight ratio of from about 1:1 to about 200:1.

46. A composition according to claim 45, comprising a cyclodextrin to protein weight ratio of from about 2:1 to about 50:1.

47. A composition according to claim 41 wherein said protein is superoxide dismutase.

48. A composition according to claim 41, wherein said protein is insulin.

49. A composition according to claim 41, wherein said protein is tissue plasminogen activator.

50. A composition according to claim 41, wherein said protein is erythropoietin.

51. A composition according to claim 41, wherein said protein is an interferon.

52. A composition according to claim 51, wherein said interferon is β-interferon.

53. A composition according to claim 41, wherein said protein is a growth hormone.

54. A composition according to claim 41, wherein said protein is epidermal growth factor.

55. A composition according to claim 41, wherein said protein is tumor necrosis factor.

56. A composition according to claim 41, wherein said protein is atrial natriuretic factor.

57. A composition according to claim 41, wherein said protein is a colony stimulating factor.

58. A composition according to claim 41, suitable for human or veterinary administration.

59. A composition according to claim 41, suitable for in vitro use.

60. A composition according to claim 39, suitable for parenteral administration.

61. A composition according to claim 58, reconstituted for parenteral administration.

62. A method for stabilizing a protein against denaturation or aggregation, said method comprising combining said protein with an effective stabilizing amount of cyclodextrin selected from the group consisting of hydroxypropyl, hydroxyethyl, glucosyl, maltosyl and maltotriosyl derivatives of β- and γ-cyclodextrin, said stabilizing amount being sufficient to prevent denaturation or aggregation of said protein, said protein being other than an interleukin, said cyclodextrin being in an aqueous solution comprising 0.1% (w/v) to 12.5% (w/v) cyclodextrin.

63. A composition comprising a protein and an effective stabilizing amount of cyclodextrin selected from the group consisting of hydroxypropyl, hydroxyethyl, glucosyl, maltosyl and maltotriosyl derivatives of β- and γ-cyclodextrin, said stabilizing amount of cyclodextrin being sufficient to prevent denaturation or aggregation of said protein, said protein being other than an interleukin, said cyclodextrin being in an aqueous solution comprising 0.1% (w/v) to 12.5% (w/v) cyclodextrin.

64. A lyophilized composition comprising a protein and an effective stabilizing amount of cyclodextrin selected from the group consisting of hydroxypropyl, hydroxyethyl, glucosyl, maltosyl and maltotriosyl derivatives of β- and γ-cyclodextrin, said stabilizing amount of cyclodextrin being sufficient to prevent denaturation or aggregation of said protein, said protein being other than an interleukin, said position being lyophilized from an aqueous solution comprising 0.1% (w/v) to 12.5% (w/v) cyclodextrin.

65. A method for stabilizing a protein against denaturation or aggregation, said method comprising combining said protein with an effective stabilizing amount of cyclodextrin selected from the group consisting of hydroxypropyl, hydroxyethyl, glucosyl, maltosyl and maltotriosyl derivatives of β- and γ-cyclodextrin, said stabilizing amount of cyclodextrin being sufficient to prevent denaturation or aggregation of said protein, said protein being superoxide dismutase, insulin, tissue plasminogen activator, erythropoietin, an interferon, a growth hormone, epidermal growth factor, tumor necrosis factor, atrial natriuretic factor or a colony stimulating factor.

66. A composition comprising a protein and an effective stabilizing amount of cyclodextrin selected from the group consisting of hydroxypropyl, hydroxyethyl, glucosyl, maltosyl and maltotriosyl derivatives of β- and γ-cyclodextrin, said stabilizing amount of cyclodextrin being sufficient to prevent denaturation or aggregation of said protein, said protein being superoxide dismutase, insulin, tissue plasminogen activator, erythropoietin, an interferon, a growth hormone, epidermal growth factor, tumor necrosis factor, atrial natriuretic factor or a colony stimulating factor.

67. A lyophilized composition comprising a protein and an effective stabilizing amount of cyclodextrin selected from the group consisting of hydroxypropyl, hydroxyethyl, glucosyl, maltosyl and maltotriosyl derivatives of β- and γ-cyclodextrin, said stabilizing amount of cyclodextrin being sufficient to prevent denaturation or aggregation of said protein, said protein being superoxide dismutase, insulin, tissue plasminogen activator, erythropoietin, an interferon, a growth hormone, epidermal growth factor, tumor necrosis factor, atrial natriuretic factor or a colony stimulating factor.

68. A method according to claim 1, wherein said cyclodextrin is in an aqueous solution comprising 0.1% (w/v) to 12.5% (w/v) cyclodextrin.

69. A composition according to claim 21, wherein said cyclodextrin is in an aqueous solution comprising 0.1% (w/v) to 12.5% (w/v) cyclodextrin.

70. A lyophilized composition according to claim 41, said composition being lyophilized from an aqueous solution comprising 0.1% (w/v) to 12.5% (w/v) cyclodextrin.

71. A method according to claim 62, wherein said cyclodextrin is hydroxypropyl-β-cyclodextrin.

72. A composition according to claim 63, wherein said cyclodextrin is hydroxypropyl-β-cyclodextrin.

73. A lyophilized composition according to claim 64, wherein said cyclodextrin is hydroxypropyl-β-cyclodextrin.

74. A method according to claim 65, wherein said cyclodextrin is hydroxypropyl-β-cyclodextrin.

75. A composition according to claim 66, wherein said cyclodextrin is hydroxypropyl-β-cyclodextrin.

76. A lyophilized composition according to claim 67, wherein said cyclodextrin is hydroxypropyl-β-cyclodextrin.

77. A method according to claim 68, wherein said cyclodextrin is hydroxypropyl-β-cyclodextrin.

78. A composition according to claim 69, wherein said cyclodextrin is hydroxypropyl-β-cyclodextrin.

79. A lyophilized composition according to claim 70, wherein said cyclodextrin is hydroxypropyl-β-cyclodextrin.

* * * * *